United States Patent
Sniegowski et al.

(10) Patent No.: US 7,364,564 B2
(45) Date of Patent: Apr. 29, 2008

(54) IMPLANT HAVING MEMS FLOW MODULE WITH MOVABLE, FLOW-CONTROLLING BAFFLE

(75) Inventors: Jeffry J. Sniegowski, Tijeras, NM (US); Paul J. McWhorter, Albuquerque, NM (US); M. Steven Rodgers, Albuquerque, NM (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 316 days.

(21) Appl. No.: 11/023,289

(22) Filed: Dec. 24, 2004

(65) Prior Publication Data

US 2005/0197613 A1   Sep. 8, 2005

Related U.S. Application Data

(63) Continuation-in-part of application No. 10/791,396, filed on Mar. 2, 2004, now abandoned, and a continuation-in-part of application No. 10/858,153, filed on Jun. 1, 2004.

(51) Int. Cl.
*A61M 1/36* (2006.01)
*C02F 1/44* (2006.01)

(52) U.S. Cl. ............................. 604/9; 604/8; 606/153; 210/85

(58) Field of Classification Search ............... 604/4.01, 604/6.09, 6.1, 7–10, 43, 65, 67, 506, 264, 604/167.01; 137/115.13; 210/85; 606/153
See application file for complete search history.

(56) References Cited

U.S. PATENT DOCUMENTS

| 3,159,161 A | 12/1964 | Ness |
| 3,788,327 A | 1/1974 | Donowitz et al. |
| 3,949,750 A | 4/1976 | Freeman |

(Continued)

FOREIGN PATENT DOCUMENTS

DE    19922623 A1    12/2000

(Continued)

OTHER PUBLICATIONS

PCT Search Report dated Nov. 10, 2006; Application No. PCT/US2006/024175.

(Continued)

*Primary Examiner*—Leslie R. Deak
(74) *Attorney, Agent, or Firm*—James J. Murtha

(57) ABSTRACT

Various embodiments of MEMS flow modules that may be disposed in a flow path (296) of a shunt (290) are disclosed, where the shunt (290) may be used to control a flow out of an anterior chamber (284) of an eye (266). One such MEMS flow module (58) has a tuning element (78) and a lower plate (70). A plurality of springs or spring-like structures (82) interconnect the tuning element (78) with the lower plate (70) in a manner that allows the tuning element (78) to move either toward or away from the lower plate (70), depending upon the pressure being exerted on the tuning element (78) by a flow through a lower flow port (74) on the lower plate (70). The tuning element (78) is disposed over this lower flow port (74) to induce a flow through the MEMS flow module (58) along a non-linear (geometrically) flow path.

35 Claims, 13 Drawing Sheets

U.S. PATENT DOCUMENTS

| | | |
|---|---|---|
| 4,014,335 A | 3/1977 | Arnold |
| 4,037,604 A | 7/1977 | Newkirk |
| 4,168,697 A | 9/1979 | Cantekin |
| 4,402,681 A | 9/1983 | Haas et al. |
| 4,634,418 A | 1/1987 | Binder |
| 4,750,901 A | 6/1988 | Molteno |
| 4,787,885 A | 11/1988 | Binder |
| 4,915,684 A | 4/1990 | MacKeen et al. |
| 4,936,825 A | 6/1990 | Ungerleider |
| 4,959,048 A | 9/1990 | Seder et al. |
| 4,968,296 A | 11/1990 | Ritch et al. |
| 5,041,081 A | 8/1991 | Odrich |
| 5,073,163 A | 12/1991 | Lippman |
| 5,092,837 A | 3/1992 | Ritch et al. |
| 5,127,901 A | 7/1992 | Odrich |
| 5,273,750 A | 12/1993 | Homiger et al. |
| 5,300,020 A | 4/1994 | L'Esperance, Jr. |
| 5,338,291 A | 8/1994 | Speckman et al. |
| 5,346,464 A | 9/1994 | Camras |
| 5,372,577 A | 12/1994 | Ungerleider |
| 5,433,701 A | 7/1995 | Rubinstein |
| 5,454,796 A | 10/1995 | Krupin |
| 5,558,630 A | 9/1996 | Fisher |
| 5,626,558 A | 5/1997 | Suson |
| 5,626,559 A | 5/1997 | Solomon |
| 5,702,414 A | 12/1997 | Richter et al. |
| 5,743,868 A | 4/1998 | Brown et al. |
| 5,807,302 A | 9/1998 | Wandel |
| 5,817,099 A | 10/1998 | Skolik et al. |
| 5,824,086 A | 10/1998 | Silvestrini |
| 5,868,697 A | 2/1999 | Richter et al. |
| 5,879,319 A | 3/1999 | Pynson et al. |
| 5,968,058 A | 10/1999 | Richter et al. |
| 6,001,386 A | 12/1999 | Ashton et al. |
| 6,007,511 A | 12/1999 | Prywes |
| 6,027,470 A | 2/2000 | Mendius |
| 6,186,974 B1 | 2/2001 | Allan et al. |
| 6,203,513 B1 | 3/2001 | Yaron et al. |
| 6,234,175 B1 | 5/2001 | Zhou et al. |
| 6,261,256 B1 | 7/2001 | Ahmed |
| 6,306,114 B1 | 10/2001 | Freeman et al. |
| 6,450,984 B1 | 9/2002 | Lynch et al. |
| 6,468,283 B1 | 10/2002 | Richter et al. |
| 6,494,857 B1 | 12/2002 | Neuhann |
| 6,508,779 B1 | 1/2003 | Suson |
| 6,510,600 B2 | 1/2003 | Yaron et al. |
| 6,533,768 B1 | 3/2003 | Hill |
| 6,544,208 B2 | 4/2003 | Ethier et al. |
| 6,544,249 B1 | 4/2003 | Yu et al. |
| 6,558,342 B1 | 5/2003 | Yaron et al. |
| 6,562,000 B2 * | 5/2003 | Thompson et al. ........... 604/48 |
| 6,589,198 B1 | 7/2003 | Soltanpour et al. |
| 6,595,945 B2 | 7/2003 | Brown |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,669,211 B2 | 12/2003 | Gonthier |
| 6,694,998 B1 * | 2/2004 | Hunnicutt ............... 137/116.3 |
| 6,699,210 B2 | 3/2004 | Williams et al. |
| 6,699,211 B2 | 3/2004 | Savage |
| 6,706,275 B1 | 3/2004 | Camp |
| 6,726,664 B2 | 4/2004 | Yaron et al. |
| 6,736,197 B2 | 5/2004 | Nozaki et al. |
| 6,736,791 B1 | 5/2004 | Tu et al. |
| 6,780,164 B2 | 8/2004 | Bergheim et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 * | 4/2005 | Brown .......................... 604/8 |
| 6,955,656 B2 | 10/2005 | Bergheim et al. |
| 6,981,958 B1 | 1/2006 | Gharib et al. |
| 7,104,406 B2 * | 9/2006 | Chen et al. ................. 210/498 |
| 7,115,118 B2 * | 10/2006 | Broden .................... 604/891.1 |
| 2002/0013546 A1 | 1/2002 | Grieshaber et al. |
| 2002/0128560 A1 | 9/2002 | Urich |
| 2002/0143284 A1 | 10/2002 | Tu et al. |
| 2002/0169130 A1 | 11/2002 | Tu et al. |
| 2002/0177856 A1 | 11/2002 | Richter et al. |
| 2002/0188308 A1 | 12/2002 | Tu et al. |
| 2003/0055372 A1 | 3/2003 | Lynch et al. |
| 2003/0060752 A1 | 3/2003 | Bergheim et al. |
| 2003/0069637 A1 | 4/2003 | Lynch et al. |
| 2003/0088260 A1 | 5/2003 | Smedley et al. |
| 2003/0181848 A1 | 9/2003 | Bergheim et al. |
| 2003/0187384 A1 | 10/2003 | Bergheim et al. |
| 2003/0187385 A1 | 10/2003 | Bergheim et al. |
| 2003/0191428 A1 | 10/2003 | Bergheim et al. |
| 2003/0220602 A1 | 11/2003 | Lynch et al. |
| 2003/0229303 A1 | 12/2003 | Haffner et al. |
| 2003/0232015 A1 | 12/2003 | Brown et al. |
| 2003/0236483 A1 | 12/2003 | Ren |
| 2004/0015140 A1 | 1/2004 | Shields |
| 2004/0024345 A1 | 2/2004 | Gharib et al. |
| 2004/0073231 A1 | 4/2004 | Juan et al. |
| 2004/0088048 A1 | 5/2004 | Richter et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0193095 A1 | 9/2004 | Shadduck |
| 2004/0210181 A1 | 10/2004 | Vass et al. |
| 2004/0225250 A1 | 11/2004 | Yablonski |
| 2004/0249333 A1 | 12/2004 | Bergheim et al. |
| 2004/0254517 A1 | 12/2004 | Quiroz-Mercado et al. |
| 2004/0254521 A1 | 12/2004 | Simon |
| 2004/0260228 A1 | 12/2004 | Lynch et al. |
| 2005/0038334 A1 | 2/2005 | Lynch et al. |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0148925 A1 | 7/2005 | Rottenberg et al. |
| 2005/0184003 A1 | 8/2005 | Rodgers et al. |
| 2005/0184004 A1 | 8/2005 | Rodgers et al. |
| 2005/0194303 A1 | 9/2005 | Sniegowski et al. |
| 2005/0197613 A1 | 9/2005 | Sniegowski et al. |
| 2005/0197653 A1 | 9/2005 | Sniegowski et al. |
| 2005/0209549 A1 | 9/2005 | Bergheim et al. |
| 2005/0209550 A1 | 9/2005 | Bergheim et al. |
| 2005/0266047 A1 | 12/2005 | Tu et al. |
| 2005/0267398 A1 | 12/2005 | Protopsaltis et al. |
| 2005/0268722 A1 | 12/2005 | Tai et al. |
| 2005/0271704 A1 | 12/2005 | Tu et al. |
| 2005/0273033 A1 | 12/2005 | Grahn et al. |
| 2005/0288617 A1 | 12/2005 | Yaron |
| 2005/0288619 A1 | 12/2005 | Gharib et al. |
| 2006/0212097 A1 * | 9/2006 | Varadan et al. ............... 607/62 |

FOREIGN PATENT DOCUMENTS

| | | |
|---|---|---|
| DE | 19922623 C2 | 10/2002 |
| WO | WO 01/50943 A2 | 7/2001 |
| WO | WO 01/50943 A3 | 7/2001 |
| WO | WO0150943 | 7/2001 |
| WO | WO 01/099175 A1 | 12/2001 |
| WO | WO 03/092564 A1 | 11/2003 |
| WO | WO 2005/081967 | 9/2005 |
| WO | WO 2005/081968 | 9/2005 |
| WO | WO2005081967 | 9/2005 |

WO  WO 2005/105197  11/2005

OTHER PUBLICATIONS

Tae Seok Sim and Yong-Kweon Kim: A Study on the Passive Microvalve Applicable to Drainage Device for Glaucoma; Journal of Semiconductor Technology and Science, vol. 2., No. 4.

Spiegel, D.; Schefthaler M.; Kobuch, K.; Outflow Facilities Through Descemet's Membrane in Rabbits; Graefes Arch Clin Exp Ophthalmol Feb. 2002; 240 (2):111-3.

[No Authors listed] Krupin Eye Value With Disk for Filtration Surgery. The Krupin Eye Valve Filtering Surgery Study Group. Ophthalmology. Apr. 1994; 101(4):651-8.

AGFID Project Team; Cell and Protein Adhesion Studies in Glaucoma Drainage Device Development; Br. J. Ophthalmol. 1999; 83; 1168-1171.

Bruce Allan; Closer to Nature: New Biomaterials and Tissue Engineering in Ophthalmology; Br. J. Ophthalmol 1999; 83; 1235-1240.

AGFID Project Team; Experimental Flow Studies in Glaucoma Drainage Device Development; Br. J. Ophthalmol 2001; 85; 1231-1236.

Yael Hanein; Y. Vickie Pan; Buddy D. Ratner; Denice D. Denton; Karl F. Bohringer; Micromachining of Non-Fouling Coatings for Bio-MEMS Applications; Sensors & Actuators B 81.

Patty Chen; Eugene Lim; Kin-Joe Sham; Adiel Smith; and Patrick Willoughby; FDA Report; Smartflow Glaucoma Stent; Jan. 9, 2003 Submitting to Myron Spector & I.V. Yannas.

K.S. Lim, B.D.S. Allan AW Lloyd, A Muir, PT Khaw; Glaucoma Drainage Devices; Past, Present and Future; Br. J. Ophthalmol 1998;82; 1083-1089.

D.J. Howorth; Feasibility Study for a Micromachined Glaucoma Drainage Device; MSc Thesis From Cranfield University 2001-2002; Sep. 13, 2002.

Cristina Rodica Neaug, A Medical Microactuator Based on an Electrochemical Principle, Sep. 4, 1966; Roemania.

* cited by examiner

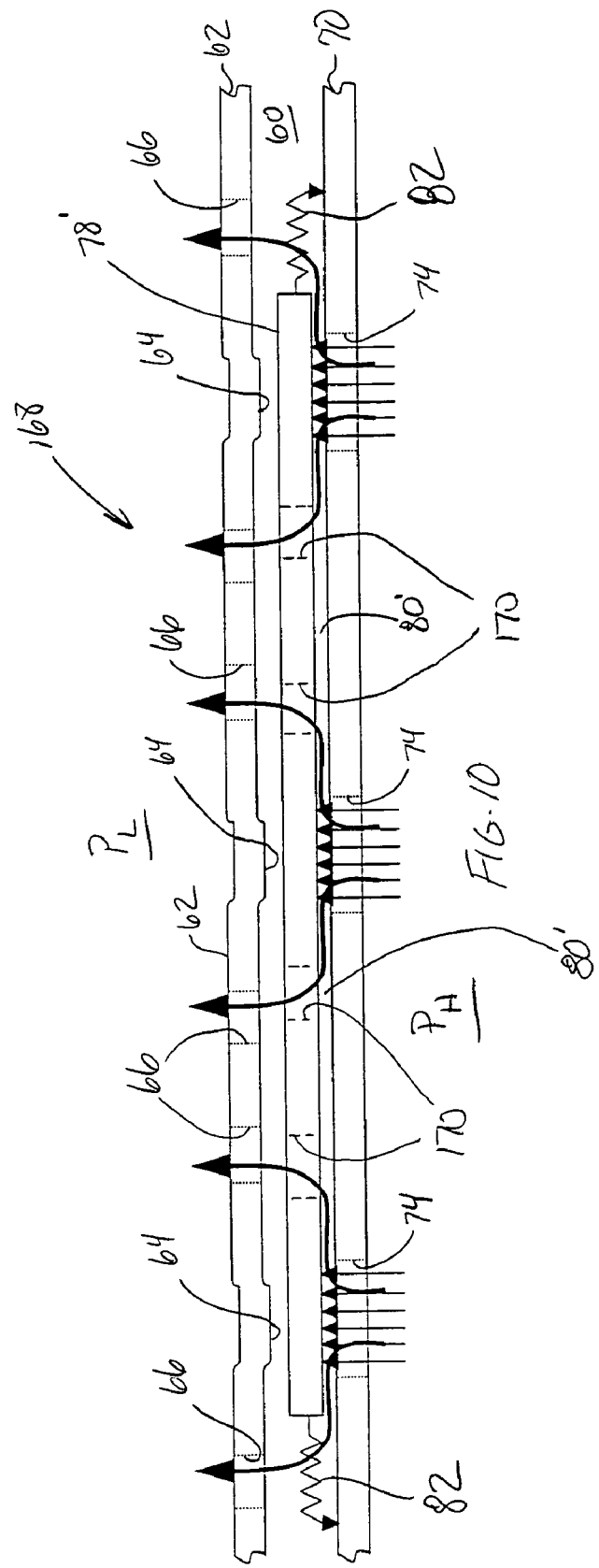

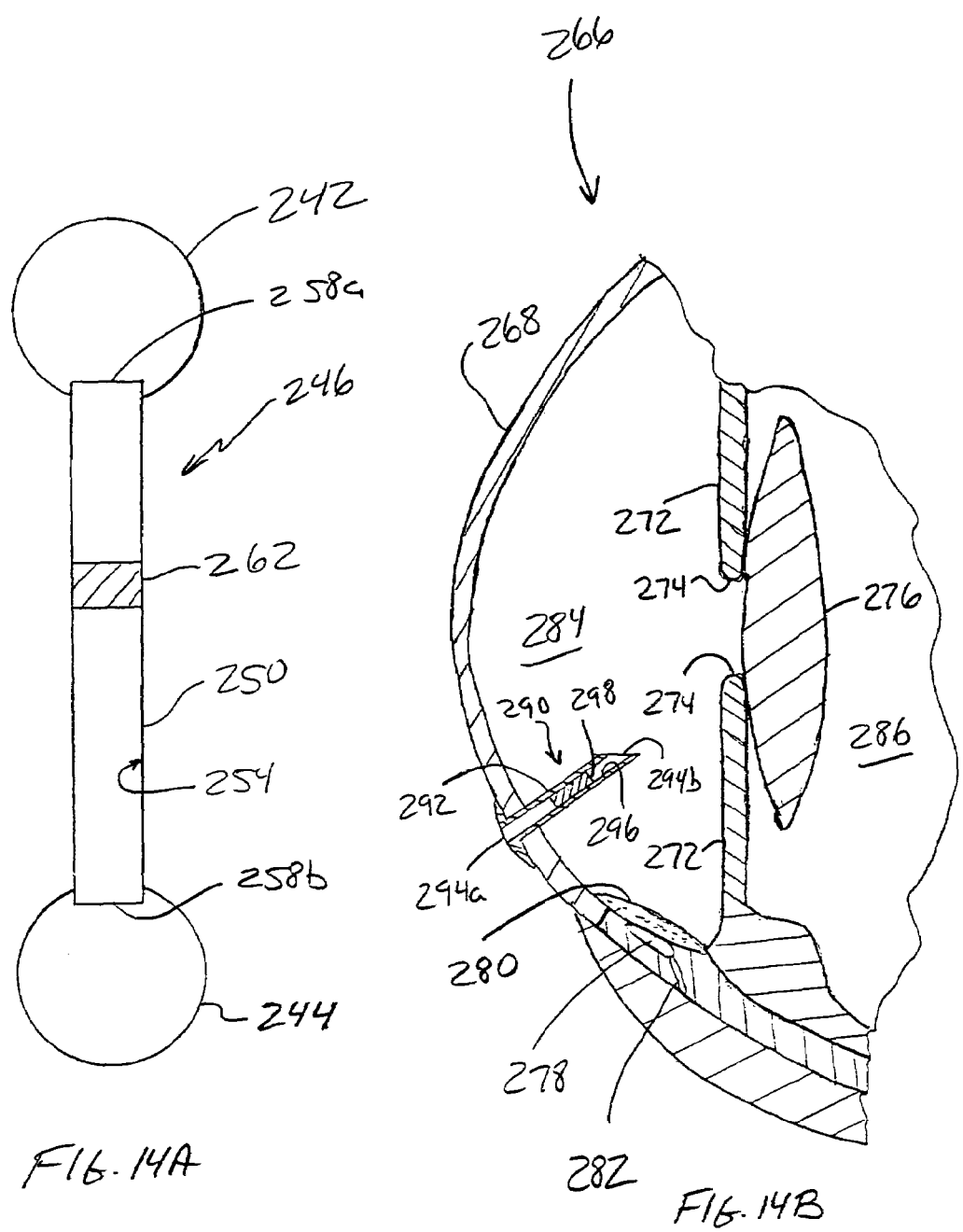

IMPLANT HAVING MEMS FLOW MODULE WITH MOVABLE, FLOW-CONTROLLING BAFFLE

CROSS-REFERENCE TO RELATED APPLICATIONS

This patent application is a continuation-in-part of, and claims priority under 35 U.S.C. § 120 to, U.S. patent application Ser. No. 10/791,396, that is entitled "MEMS FLOW MODULE WITH FILTRATION AND PRESSURE REGULATION CAPABILITIES," that was filed on Mar. 2, 2004 now abandoned, and the entire disclosure of which is incorporated by reference in its entirety herein. This patent application is also a continuation-in-part of, and claims priority under 35 U.S.C. § 120 to, U.S. patent application Ser. No. 10/858,153, that is entitled "FILTER ASSEMBLY WITH MICROFABRICATED FILTER ELEMENT," and that was filed on Jun. 1, 2004.

FIELD OF THE INVENTION

The present invention generally relates to the field of microfabricated devices and, more particularly, to an implant having a microfabricated or MEMS flow module, that in turn uses a movable baffle to control the flow through the MEMS flow module.

BACKGROUND OF THE INVENTION

High internal pressure within the eye can damage the optic nerve and lead to blindness. There are two primary chambers in the eye—an anterior chamber and a posterior chamber that are generally separated by a lens. Aqueous humor exists within the anterior chamber, while vitreous humor exists in the posterior chamber. Generally, an increase in the internal pressure within the eye is caused by more fluid being generated within the eye than is being discharged by the eye. The general consensus is that it is the fluid within the anterior chamber of the eye that is the main contributor to an elevated intraocular pressure.

One proposed solution to addressing high internal pressure within the eye is to install an implant. Implants are typically directed through a wall of the patient's eye so as to fluidly connect the anterior chamber with an exterior location on the eye. There are a number of issues with implants of this type. One is the ability of the implant to respond to changes in the internal pressure within the eye in a manner that reduces the potential for damaging the optic nerve. Another is the ability of the implant to reduce the potential for bacteria and the like passing through the implant and into the interior of the patient's eye.

BRIEF SUMMARY OF THE INVENTION

A first aspect of the present invention is generally directed to a filter assembly. This filter assembly includes a first housing, a second housing, and a MEMS filter element. The second housing is at least partially disposed within the first housing and includes a first flow path. The MEMS filter element is mounted to the second housing such that all flow through the first flow path is directed through the MEMS filter element.

Various refinements exist of the features noted in relation to the first aspect of the present invention. Further features may also be incorporated in the first aspect of the present invention as well. These refinements and additional features may exist individually or in any combination. The filter assembly may be used for any appropriate application, such as in an implant. The first housing may be of any appropriate size and/or configuration, and further may be formed from any material or combination of materials. For instance, the first housing may be a rigid body, a deformable body, or formed from a combination of rigid and deformable components.

The second housing used by the first aspect may provide structural integrity for the MEMS filter element. For instance, the second housing may be a rigid structure, or at least may be more rigid than the MEMS filter element. Representative materials from which the second housing may be formed include without limitation polymethylmethacrylate (PMMA), titanium, and other implantable metals and plastics. The second housing may be of any appropriate shape (e.g., a cylinder), but will typically be adapted in some manner for disposition at least partially within the first housing. In this regard, the first housing may be disposed about the second housing along the entire length of the second housing (e.g., each end of the second housing may be flush with or recessed inwardly from the corresponding end of the first housing), or only along a portion of the length of the second housing (e.g., one or both ends of the second housing may extend beyond the corresponding end of the first housing).

The second housing is preferably maintained in a stationary or fixed position relative to the first housing in the case of the first aspect. For instance, the second housing may be bonded to the first housing, a press fit may be utilized between the first and second housing, the first housing may be shrink-fitted about the second housing, or any combination thereof. A third housing may also be at least partially disposed within the first housing, with the MEMS filter element being located between adjacent ends of the second and third housings and preferably mounted to at least one of the second and third housings. Such a third housing is also preferably maintained in a stationary or fixed position relation to the first housing in the same manner as the second housing.

The MEMS filter element used by the first aspect may provide one or more functions in addition to filtering (e.g., pressure regulation). Multiple locations may be appropriate in relation to the MEMS filter element. For instance, the MEMS filter element may be recessed within the second housing. Consider the case with the second housing includes first and second ends, and where the first flow path extends between these first and second ends. The MEMS filter element may be located anywhere between these first and second ends. Another option would be for the MEMS filter element to be mounted on the first or second end of the second housing.

Any appropriate way of mounting the MEMS filter element to the second housing may be used in the case of the first aspect. For instance, the MEMS filter element may be bonded to second housing, there may be a press fit between the MEMS filter element and the second housing, or both. In any case, preferably the MEMS filter element is maintained in a fixed position relative to the second housing.

A second aspect of the present invention is directed to a MEMS flow module. This MEMS flow module includes a first flow port and a movable tuning element. The position of the tuning element is dependent at least in part upon a pressure being exerted on the tuning element by a flow entering the MEMS flow module through the first flow port, while a flow rate of a flow exiting the MEMS flow module in turn is dependent upon a position of the tuning element.

Various refinements exist of the features noted in relation to the second aspect of the present invention. Further features may also be incorporated in the second aspect of the present invention as well. These refinements and additional features may exist individually or in any combination. The MEMS flow module is preferably a passive device (no external signal of any type required) and may be used for any appropriate application. For instance, the MEMS flow module may be disposed in a flow path of any type (e.g., between a pair of sources of any appropriate type, such as a man-made reservoir, a biological reservoir, and/or the environment). That is, the MEMS flow module could be disposed in a conduit that fluidly interconnects multiple sources (e.g., two or more), and each source may be either a man-made reservoir, a biological reservoir, the environment, or any other appropriate source. One example would be to dispose the MEMS flow module in a conduit extending between the anterior chamber of an eye and a location that is exterior of the cornea of the eye. Another example would be to dispose the MEMS flow module in a conduit extending between the anterior chamber of an eye and another location that is exterior of the sclera of the eye. Yet another example would be to dispose the MEMS flow module in a conduit extending between the anterior chamber of an eye and another location within the eye (e.g., into Schlemm's canal) or body. In any case, the MEMS flow module could be disposed directly into such a conduit, or one or more housings could be used to integrate the MEMS flow module with the conduit (e.g., in accordance with the first aspect, where the MEMS flow module of the second aspect would replace the above-noted MEMS filter element).

In one embodiment of the second aspect, movement of the tuning element provides pressure regulation capabilities. In another embodiment, the MEMS flow module provides pressure regulation for a flow through the MEMS flow module in a first direction, and filters a flow through the MEMS flow module in a second direction that is opposite the first direction. Consider the case where the MEMS flow module is used in an implant to relieve intraocular pressure in a patient's eye, and where the MEMS flow module is disposed in a flow path between the anterior chamber of the patient's eye and another location (e.g., exteriorly of the eye or somewhere else within the eye, such as Schlemm's canal). The MEMS flow module may be used to regulate the flow of fluid out of the anterior chamber of the patient's eye in a manner that regulates the pressure in the anterior chamber in a desired manner, and may filter any "backflow" through the MEMS flow module that would be directed into this anterior chamber. The MEMS flow module may be designed for a laminar flow therethrough in this and other instances, although the MEMS flow module may be applicable to a turbulent flow therethrough as well.

The MEMS flow module of the second aspect may include a first plate, that in turn includes the first flow port. The first flow port through the first plate may be of any appropriate size and/or shape. Preferably, the first plate is parallel with a surface of the tuning element that faces away from the first plate (at least the general lateral extent of the tuning element). In one embodiment, the tuning element is always disposed in spaced relation to the first plate. Another embodiment has the tuning element disposed on the first plate until the flow through the first flow port exerts at least a certain pressure on the tuning element to move the tuning element away from the first plate.

At least one spring may be used to movably interconnect the tuning element with the above-noted first plate in the case of the second aspect. Each such spring may be of any appropriate size and/or configuration, but should be less rigid than the tuning element. Multiple springs will typically be used to allow the tuning element to at least substantially maintain its orientation when moving in response to a change in the pressure of the flow entering the MEMS flow module through the first flow port.

A first flow channel may be defined by a space between the tuning element and the above-noted first plate in the case of the second aspect. The flow entering the MEMS flow module through the first flow port may be redirected by the first tuning element into this first flow channel. This first flow channel may extend at least generally in the lateral dimension, including at a right angle to the direction of the flow entering the MEMS flow module through the first flow port. In any case, the flow path through the MEMS flow module is preferably non-linear (geometrically) as a result of the tuning element inducing at least one change in direction for a flow through the MEMS flow module.

The above-noted first flow channel may always have a volume greater than zero in the case of the second aspect. At least one dimension of this first flow channel may be selected to provide a filter trap for a flow proceeding through the first flow channel in the direction of the first flow port. The spacing between the tuning element at its perimeter and an underlying first plate having the associated first flow port(s) may provide this filter trap. Another option is to include an annular filter wall that extends down from the tuning element in the direction of any underlying first plate. Any such annular filter wall is preferably dimensioned such that that when this annular filter wall is projected onto the first plate, the resulting area encompasses the first flow port. Multiple annular filter walls of this type may be used for the case where multiple first flow ports are associated with the tuning element (e.g., each first flow port preferably has an associated annular filter wall). Any appropriate type/configuration of filter walls may be used to provide a controlled gap for a flow attempting to exit the MEMS flow module through the first flow port.

The above-noted first plate in the case of the second aspect may include a first group of a plurality of first flow ports, with the tuning element being aligned with each first flow port in this first group. That is, a flow through multiple first flow ports may collectively act upon the tuning element. The flow through any first flow port in the first group may be required to proceed around a perimeter of the tuning element before exiting the MEMS flow module. One or more tuning element flow ports may extend through the tuning element as well. The plurality of first flow ports and the plurality of tuning element flow ports are preferably arranged such that a flow through any given first flow port must change direction to flow through any of the tuning element flow ports. One or more tuning element flow ports could be implemented for the case where a given tuning element only utilizes a single first flow port as well (e.g., where the pressure acting on a tuning element is primarily from a flow through a single first flow port).

The pressure exerted on the tuning element by a flow through the first flow port has an effect on the position of the tuning element relative to the first flow port in the case of the second aspect. The position of the tuning element in turn determines the flow rate out of the MEMS flow module. Generally, the flow rate out of the MEMS flow module may increase as the spacing between the tuning element and the first flow port increases, and may decrease as the spacing between the tuning element and the first flow port decreases. There are a number of characterizations that may be made in relation to the tuning element in this regard. One is that the tuning element is preferably positioned such that a flow proceeding into the MEMS flow module through the first flow port will contact the tuning element (e.g., the streamlines of this flow will intersect the tuning element). Further in this regard, the tuning element is positioned such that this flow preferably acts orthogonally on the tuning element (e.g., the force exerted on the tuning element from this flow is "normal" to the corresponding surface of the tuning element). The position of the tuning element is dependent upon (at least partially for the case where there are multiple first flow ports associated with the tuning element, and possibly entirely where the tuning element is associated with a single first flow port) the pressure being exerted on the tuning element by a flow entering the MEMS flow module through the first flow port. At least a certain increase in this pressure will move the tuning element further away from the first flow port (e.g., increasing the size of the above-noted first flow channel), while subsequent decreases in this pressure will move the tuning element closer to the first flow port (e.g., reducing the size of the above-noted first flow channel).

The above-noted movement of the tuning element in response to pressure changes is itself subject to a number of characterizations. One is that the orientation of the tuning element is preferably at least substantially maintained during this movement. Another is that the tuning element moves only at least substantially axially. Another is that the distance between the tuning element and any underlying first plate changes by at least substantially the same amount across the entirety of the surface of the tuning element that faces the upper surface of this first plate. Yet another is that the cross-sectional area of the above-noted first flow channel (the space between the tuning element and the first plate having at least one first flow port) changes proportionally in the lateral dimension or along the "length" of the first flow channel.

The MEMS flow module of the second aspect may include a plurality of tuning elements of the above-noted type, each having at least one associated first flow port. Each of these tuning elements may be independently mounted on a common first plate by at least one, and more preferably a plurality of springs. The MEMS flow module may also include a second plate that is disposed in spaced relation to the tuning element(s) in a direction in which the tuning element(s) moves in response to an increase in pressure thereon from a flow through the corresponding first flow port(s). Any such second plate preferably includes at least one, and more preferably a plurality of second flow ports. This second plate may be anchored to a first plate having each first flow port for each tuning element used by the MEMS flow module. Preferably at least one annular support (e.g., any configuration that extends a full 360 degrees about a reference axis to define a closed perimeter) interconnects any such first and second plates, with all first flow ports and all second flow ports preferably being positioned inwardly of this annular support. This second plate may include at least one overpressure stop for each tuning element to limit the maximum spacing between the tuning element and the first plate. Instead of the tuning element being movably interconnected by one or more springs that are anchored to the first plate, each such spring could be anchored to the second plate. Another option would be for one or more springs to extend between the tuning element and the first plate, and for one or more springs to extend between the tuning element and second plate to allow the tuning element to move for flow control purposes.

A third aspect is directed to a method for regulating a fluidic output from a first source. A fluid from a first source is directed through a MEMS flow module and to a second source. The pressure of the first source is regulated by the MEMS flow module in a manner such that an increase in a flow rate out of the MEMS flow module is proportionally greater than an increase in a differential pressure across the MEMS flow module. The MEMS flow module also filters a continually open flow path through the MEMS flow module that is fluidly connected with the first source. A constituent that enters the MEMS flow module from the second source, that is at least of a first size, and that is attempting to proceed along the flow path through the MEMS flow module back toward the first source, is retained within the MEMS flow module.

Various refinements exist of the features noted in relation to the third aspect of the present invention. Further features may also be incorporated in the third aspect of the present invention as well. These refinements and additional features may exist individually or in any combination. The first and second sources each may be of any appropriate type, size, and configuration (e.g., man-made, biological, the environment). In one embodiment, the first source is an anterior chamber of a patient's eye, and the second source is another appropriate location, such as the environment or externally of the eye, or another location within the eye (e.g., Schlemm's canal) or body. The MEMS flow module of the second aspect may be used in relation to this third aspect.

A fourth aspect of the present invention is directed to an implant for addressing pressure within a first body region. The implant includes a conduit having a flow path and is adapted to fluidly interconnect with the first body region. A MEMS flow module is disposed within the flow path and includes a flow regulator, that in turn includes a first baffle or tuning element. The MEMS flow module also includes a first plate. A first flow port extends through the first plate, and the first baffle is aligned with the first flow port. The first baffle is movable relative to the first plate to change the magnitude of a spacing of the first baffle from the first plate in response to a change in differential pressure across the MEMS flow module.

Various refinements exist of the features noted in relation to the fourth aspect of the present invention. Further features may also be incorporated in the fourth aspect of the present invention as well. These refinements and additional features may exist individually or in any combination. The implant may be used for any appropriate application. One example would be to adapt the conduit to extend between the anterior chamber of an eye and a location that is exterior of the cornea of the eye. Another example would be to adapt the conduit to extend between the anterior chamber of an eye and another location that is exterior of the sclera of the eye. Yet another example would be to adapt the conduit to extend between the anterior chamber of an eye and another location within the eye (e.g., into Schlemm's canal) or body.

The conduit used by the fourth aspect may be of any appropriate configuration for the particular implant application, as may be the MEMS flow module. Any way of integrating the MEMS flow module with the conduit may be used, including using one or more housings, such as in accordance with the first aspect (where the MEMS flow module of this fourth aspect would replace the MEMS filter element discussed in relation to the first aspect). The MEMS flow module may be retained within the flow path of the conduit in any appropriate manner as well. Preferably, the MEMS flow module is a passive device (no external signal of any type required). Any appropriate coating may be applied to various surfaces of the MEMS flow module and/or any housing associated therewith, including without limitation a coating that improves biocompatibility, that makes such surfaces more hydrophilic, and/or that reduces the potential for bio-fouling. In one embodiment, a self assembled monolayer coating (e.g., poly-ethylene-glycol) is applied in any appropriate manner (e.g., liquid or vapor phase, with vapor phase being the preferred technique) to all exposed surfaces of the MEMS flow module and any housing that integrates the MEMS flow module for positioning within the conduit. Coatings of this type may be used in relation to the other aspects of the present invention described herein as well.

Surface micromachining is the preferred technology for fabricating the MEMS flow module of the fourth aspect. In this regard, the MEMS flow module may be fabricated in at least two different levels that are spaced from each other (hereafter a first fabrication level and a second fabrication level). The first baffle or tuning element may be fabricated at least in the first fabrication level, while the first plate may be fabricated in at least the second fabrication level. It should be appreciated that the characterization of the first baffle being in a "first fabrication level" and the first plate being in the "second fabrication level" by no means requires that the first fabrication level be that which is deposited "first", and that the second fabrication level be that which is deposited "second." Moreover, it does not require that the first fabrication level and the second fabrication level be immediately adjacent. In one embodiment, the MEMS flow module is fabricated on an appropriate substrate and where the first plate is fabricated in one structural layer that is disposed somewhere between the substrate and another structural layer in which the first baffle is fabricated.

One or both of the first baffle and the first plate each may exist in a single fabrication level or may exist in multiple fabrication levels. "Fabrication level" corresponds with what may be formed by a deposition of a structural material before having to form any overlying layer of a sacrificial material (e.g., from a single deposition of a structural layer or film). In the above-noted first instance, a deposition of a structural material in a single fabrication level may define an at least generally planar layer. Another option regarding the first instance would be for the deposition of a structural material in a single fabrication level to define an at least generally planar portion, plus one or more structures that extend down toward, but not to, the underlying structural layer at the underlying fabrication level. In either situation and prior to an etch release, in at least some cases there will be at least some thickness of sacrificial material disposed between the entirety of the first baffle and the first plate.

In the above-noted second instance, two or more structural layers or films from adjacent fabrication levels could be disposed in direct interfacing relation (e.g., one directly on the other). Over the region that is to define the first baffle or first plate, this would require removal of the sacrificial material that is deposited on the structural material at one fabrication level before depositing the structural material at the next fabrication level. Another option regarding the above-noted second instance would be to maintain the separation between structural layers or films in different fabrication levels for the first baffle and/or first plate, but provide an appropriate structural interconnection therebetween (e.g., a plurality of columns, posts, or the like extending between adjacent structural layers or films in different, spaced fabrication levels).

In one embodiment of the fourth aspect, movement of the first baffle provides pressure regulation capabilities. In another embodiment, the MEMS flow module provides pressure regulation for a flow through the MEMS flow module in a first direction, and filters a flow through the MEMS flow module in a second direction that is opposite the first direction. Consider the case where the implant is being used to relieve intraocular pressure in a patient's eye, and where the MEMS flow module is disposed in a flow path between the anterior chamber of the patient's eye and another location (e.g., exteriorly of the eye, or somewhere else within the eye or body). The MEMS flow module may be used to regulate the flow of fluid out of the anterior chamber of the patient's eye in a manner that regulates the pressure in the anterior chamber in a desired manner, and may filter any "backflow" through the MEMS flow module that would be directed into this anterior chamber. The MEMS flow module may be designed for a laminar flow therethrough in this and other instances, although the MEMS flow module may be applicable to a turbulent flow therethrough as well.

The MEMS flow module of the fourth aspect includes the first plate, that in turn includes the first flow port. The first flow port through the first plate may be of any appropriate size and/or shape. Preferably, the first plate is parallel with a surface of the first baffle that faces away from the first plate (at least the general lateral extent of the first baffle). In one embodiment, the first baffle is always disposed in spaced relation to the first plate. Another embodiment has the first baffle disposed on the first plate until the flow through the first flow port exerts at least a certain pressure on the first baffle to move the first baffle away from the first plate. That is, even though the first baffle and the first plate may be fabricated in different, spaced levels, one or more biasing springs or the like could be fabricated and configured to bias the first baffle against the first plate (and over the first flow port(s)) until a certain differential pressure exists across the MEMS flow module, at which time the first baffle would then move away from the first plate. Therefore, "changing a magnitude of the spacing" between the first baffle and the first plate in response to a change in differential pressure across the MEMS flow module contemplates the first baffle originally being in contact with the first plate and thereafter moving away from the first plate.

At least one spring may be used to movably interconnect the first baffle with the above-noted first plate in the case of the fourth aspect. Each such spring may be of any appropriate size and/or configuration, but should be less rigid than the first baffle. Multiple springs will typically be used to allow the first baffle to at least substantially maintain its orientation when moving in response to a change in the pressure of the flow entering the MEMS flow module through the first flow port.

A first flow channel may be defined by a space between the first baffle and the above-noted first plate in the case of the fourth aspect. The flow entering the MEMS flow module through the first flow port may be redirected by the first baffle into this first flow channel. This first flow channel may extend at least generally in the lateral dimension, including at a right angle to the direction of the flow entering the MEMS flow module through the first flow port. In any case, the flow path through the MEMS flow module is preferably non-linear (geometrically) as a result of the first baffle inducing at least one change in direction for a flow through the MEMS flow module.

The above-noted first flow channel may always have a volume greater than zero in the case of the fourth aspect. At least one dimension of this first flow channel may be selected to provide a filter trap for a flow proceeding through the first flow channel in the direction of the first flow port. The spacing between the first baffle at its perimeter and the underlying first plate having the associated first flow port(s) may provide this filter trap. Another option is to include an annular filter wall that extends down from the first baffle in the direction of the underlying first plate. Any such annular filter wall is preferably dimensioned such that that when this annular filter wall is projected onto the first plate, the resulting area encompasses the first flow port. Multiple annular filter walls of this type may be used for the case where multiple first flow ports are associated with the first baffle (e.g., each first flow port preferably has an associated annular filter wall). Any appropriate type/configuration of filter walls may be used to provide a controlled gap for a flow attempting to exit the MEMS flow module through the first flow port.

The above-noted first plate in the case of the fourth aspect may include a first group of a plurality of first flow ports, with the first baffle being aligned with each first flow port in this first group. That is, a flow through multiple first flow ports may collectively act upon the first baffle. The flow through any first flow port in the first group may be required to proceed around a perimeter of the first baffle before exiting the MEMS flow module. One or more baffle flow ports may extend through the first baffle as well. The plurality of first flow ports and the plurality of baffle flow ports are preferably arranged such that a flow through any given first flow port must change direction to flow through any of the baffle flow ports. One or more baffle flow ports could be implemented for the case where a given first baffle only utilizes a single first flow port as well (e.g., where the pressure acting on the first baffle is primarily from a flow through a single first flow port).

The pressure exerted on the first baffle by a flow through the first flow port may have an effect on the position of the first baffle relative to the first flow port in the case of the fourth aspect. The position of the first baffle in turn may determine the flow rate out of the MEMS flow module. Generally, the flow rate out of the MEMS flow module may increase as the spacing between the first baffle and the first flow port increases, and may decrease as the spacing between the first baffle and the first flow port decreases. There are a number of characterizations that may be made in relation to the first baffle in this regard. One is that the first baffle is preferably positioned such that a flow proceeding into the MEMS flow module through the first flow port will contact the first baffle (e.g., the streamlines of this flow will intersect the first baffle). Further in this regard, the first baffle is positioned such that this flow preferably acts orthogonally on the first baffle (e.g., the force exerted on the first baffle from this flow is "normal" to the corresponding surface of the first baffle). The position of the first baffle is dependent upon (at least partially for the case where there are multiple first flow ports associated with the first baffle, and possibly entirely where the first baffle is associated with a single first flow port) the pressure being exerted on the first baffle by a flow entering the MEMS flow module through the first flow port. At least a certain increase in this pressure will move the first baffle further away from the first flow port (e.g., increasing the size of the above-noted first flow channel), while subsequent decreases in this pressure will move the first baffle closer to the first flow port (e.g., reducing the size of the above-noted first flow channel).

The above-noted movement of the first baffle in response to pressure changes is itself subject to a number of characterizations. One is that the orientation of the first baffle is preferably at least substantially maintained during this movement. Another is that the first baffle moves only at least substantially axially (e.g., along an axis that corresponds with a direction of a flow entering the MEMS flow module through the first flow port). Another is that the distance between the first baffle and any underlying first plate changes by at least substantially the same amount across the entirety of the surface of the first baffle that faces the upper surface of this first plate. Yet another is that the cross-sectional area of the above-noted first flow channel (the space between the first baffle and the first plate having at least one first flow port) changes proportionally in the lateral dimension or along the "length" of the first flow channel.

The MEMS flow module of the fourth aspect may include a plurality of first baffles of the above-noted type, each having at least one first flow port. Each of these first baffles may be independently mounted on a common first plate by at least one, and more preferably a plurality of springs. The MEMS flow module may also include a second plate that is disposed in spaced relation to first baffle(s) in a direction in which the first baffle(s) moves in response to an increase in pressure thereon from a flow through the corresponding first flow port(s). Any such second plate preferably includes at least one, and more preferably a plurality of second flow ports. This second plate may be anchored to a first plate having each first flow port for each first baffle used by the MEMS flow module. Preferably at least one annular support (e.g., any configuration that extends a full 360 degrees about a reference axis to define a closed perimeter) interconnects any such first and second plates, with all first flow ports and all second flow ports preferably being positioned inwardly of this annular support. This second plate may include at least one overpressure stop for each first baffle to limit the maximum spacing between the first baffle and the first plate. Instead of the first baffle being movably interconnected by one or more springs that are anchored to the first plate, each such spring could be anchored to the second plate. Another option would be for one or more springs to extend between the first baffle and the first plate, and for one or more springs to extend between the first baffle and second plate to allow the first baffle to move for flow control purposes.

In summary, the first baffle used by the fourth aspect controls the flow through the MEMS flow module, and this flow control is subject to a number of characterizations. One is that the position of the first baffle is dependent upon a pressure being exerted on the first baffle by a flow entering the MEMS flow module through the first flow port, and a flow rate of a flow exiting the MEMS flow module is dependent upon the position of the first baffle. Another is that the first baffle is configured and moves relative to the first plate so as to provide greater than a proportional increase in the flow rate out of the MEMS flow module (at least a portion of the flow entering the MEMS flow module through the first flow port) for an increase in differential pressure across the MEMS flow module.

BRIEF DESCRIPTION OF THE SEVERAL VIEWS OF THE DRAWING

FIGS. 6-10 are each cutaway, side views of various embodiment of MEMS flow modules that may be incorporated by the MEMS flow module of FIGS. 5A-B, with FIG. 7B being a top, plan view of a portion of the MEMS flow module of FIG. 7A to illustrate one of its annular filter walls.

FIG. 14A is a schematic of one embodiment of an implant that may use any of the MEMS flow modules with a movable baffle or tuning element described herein.

FIG. 14B is a cross-sectional view of one embodiment of an implant or shunt that is used to relieve pressure within the anterior chamber of the eye, and that may utilize any of the MEMS flow modules with a movable baffle or tuning element described herein.

DETAILED DESCRIPTION OF THE INVENTION

The present invention will now be described in relation to the accompanying drawings that at least assist in illustrating its various pertinent features. Generally, the devices described herein are microfabricated. There are a number of microfabrication technologies that are commonly characterized as "micromachining," including without limitation LIGA (Lithographie, Galvonoformung, Abformung), SLIGA (sacrificial LIGA), bulk micromachining, surface micromachining, micro electrodischarge machining (EDM), laser micromachining, 3-D stereolithography, and other techniques. Hereafter, the term "MEMS device", "microfabricated device," or the like means any such device that is fabricated using a technology that allows realization of a feature size of 10 microns or less.

Figure 1:
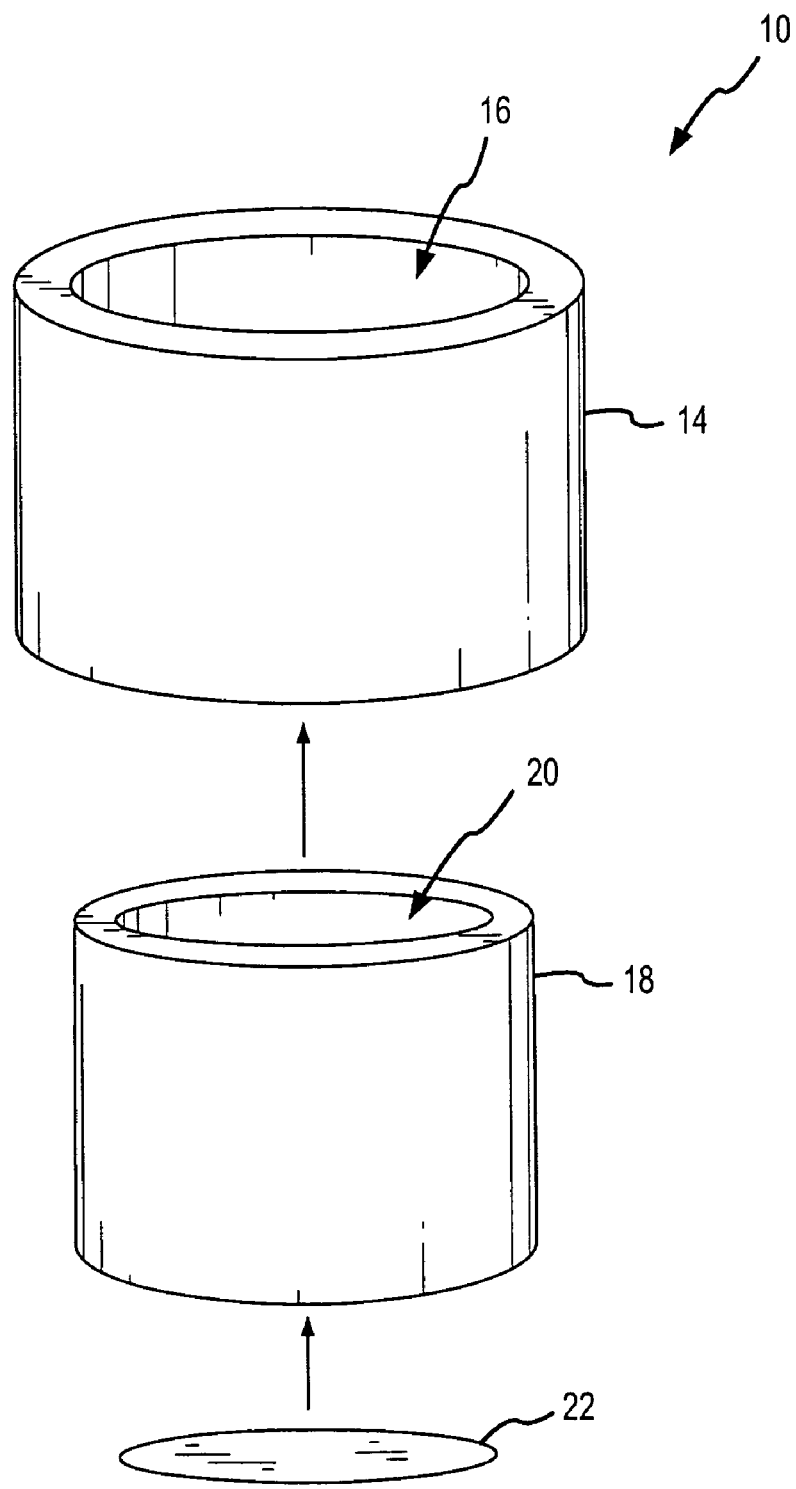
FIG. 1 is an exploded, perspective view of one embodiment of a flow assembly that uses a MEMS flow module.
Figure 2:
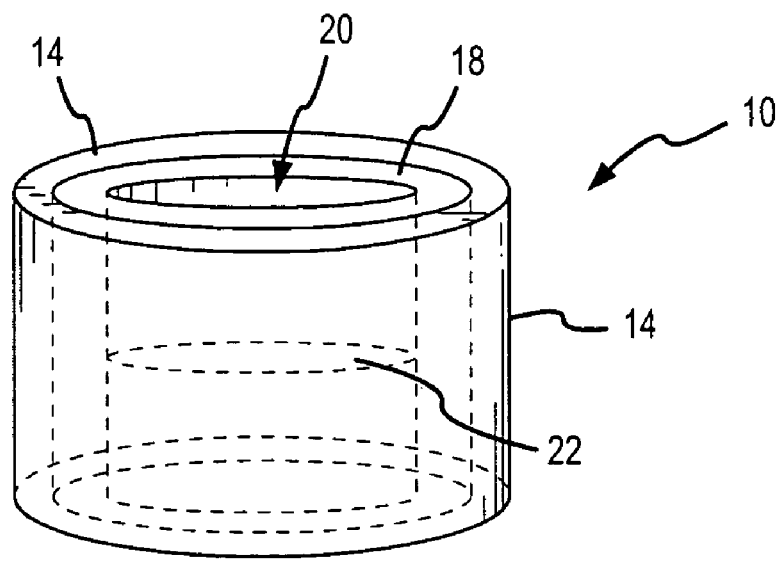
FIG. 2 is a perspective view of the flow assembly of FIG. 1 in an assembled condition.

FIGS. 1-2 schematically represent one embodiment of a flow assembly 10 that may be used for any appropriate application (e.g., the flow assembly 10 may be disposed in a flow of any type, may be used to filter and/or control the flow of a fluid of any type, may be located in a conduit that fluidly interconnects multiple sources of any appropriate type (e.g., between multiple fluid or pressure sources (including where one is the environment), such as a man-made reservoir, a biological reservoir, the environment, or any other appropriate source, or any combination thereof). One example would be to dispose the flow assembly 10 in a conduit extending between the anterior chamber of an eye and a location that is exterior of the cornea of the eye. Another example would be to dispose the flow assembly 10 in a conduit extending between the anterior chamber of an eye and another location that is exterior of the sclera of the eye. Yet another example would be to dispose the flow assembly 10 in a conduit extending between the anterior chamber of an eye and another location within the eye (e.g., into Schlemm's canal) or body.

Components of the flow assembly 10 include an outer housing 14, an inner housing 18, and a MEMS flow module 22. The position of the MEMS flow module 22 and the inner housing 18 are at least generally depicted within the outer housing 14 in FIG. 2 to show the relative positioning of these components in the assembled condition—not to convey that the outer housing 14 needs to be in the form of a transparent structure. All details of the MEMS flow module 22 and the inner housing 18 are not necessarily illustrated in FIG. 2.

The MEMS flow module 22 is only schematically represented in FIGS. 1-2, and provides at least one of a filtering function and a pressure or flow regulation function. The MEMS flow module 22 may be of any appropriate design, size, shape, and configuration, and further may be formed from any material or combination of materials that are appropriate for use by the relevant microfabrication technology. Any appropriate coating or combination of coatings may be applied to exposed surfaces of the MEMS flow module 22 as well. For instance, a coating may be applied to improve the biocompatibility of the MEMS flow module 22, to make the exposed surfaces of the MEMS flow module 22 more hydrophilic, to reduce the potential for the MEMS flow module 22 causing any bio-fouling, or any combination thereof. In one embodiment, a self assembled monolayer coating (e.g., poly-ethylene-glycol) is applied in any appropriate manner (e.g., liquid or vapor phase, with vapor phase being the preferred technique) to all exposed surfaces of the MEMS flow module 22. The main requirement of the MEMS flow module 22 is that it is a MEMS device.

The primary function of the outer housing 14 and inner housing 18 is to provide structural integrity for the MEMS flow module 22 or to support the MEMS flow module 22, and further to protect the MEMS flow module 22. In this regard, the outer housing 14 and inner housing 18 each will typically be in the form of a structure that is sufficiently rigid to protect the MEMS flow module 22 from being damaged by the forces that reasonably could be expected to be exerted on the flow assembly 10 during its assembly, as well as during use of the flow assembly 10 in the application for which it was designed.

The inner housing 18 includes a hollow interior or a flow path 20 that extends through the inner housing 18 (between its opposite ends in the illustrated embodiment). The MEMS flow module 22 may be disposed within the flow path 20 through the inner housing 18 in any appropriate manner and at any appropriate location within the inner housing 18 (e.g., at any location so that the inner housing 18 is disposed about the MEMS flow module 22). Preferably, the MEMS flow module 22 is maintained in a fixed position relative to the inner housing 18. For instance, the MEMS flow module 22 may be attached or bonded to an inner sidewall or a flange formed on this inner sidewall of the inner housing 18, a press-fit could be provided between the inner housing 18 and the MEMS flow module 22, or a combination thereof. The MEMS flow module 22 also could be attached to an end of the inner housing 18 in the manner of the embodiment of FIGS. 4A-B that will be discussed in more detail below.

The inner housing 18 is at least partially disposed within the outer housing 14 (thereby encompassing having the outer housing 14 being disposed about the inner housing 18 along the entire length of the inner housing 18, or only along a portion of the length of the inner housing 18). In this regard, the outer housing 14 includes a hollow interior 16 for receiving the inner housing 18, and possibly to provide other appropriate functionality (e.g., a flow path fluidly connected with the flow path 20 through the inner housing 18). The outer and inner sidewalls of the outer housing 14 may be cylindrical or of any other appropriate shape, as may be the outer and inner sidewalls of the inner housing 18. The inner housing 18 may be retained relative to the outer housing 14 in any appropriate manner. For instance, the inner housing 18 may be attached or bonded to an inner sidewall of the outer housing 14, a press-fit could be provided between the inner housing 18 and the outer housing 14, a shrink fit could be provided between the outer housing 14 and the inner housing 18, or a combination thereof.

The inner housing 18 is likewise only schematically represented in FIGS. 1-2, and it may be of any appropriate shape/configuration, of any appropriate size, and formed from any material or combination of materials (e.g., polymethylmethacrylate (PMMA), titanium, and other implantable metals and plastics). Typically its outer contour will be adapted to match the inner contour of the outer housing 14 in which it is at least partially disposed. In one embodiment, the illustrated cylindrical configuration for the inner housing 18 is achieved by cutting an appropriate length from hypodermic needle stock. The inner housing 18 also may be fabricated into the desired/required shape (e.g., using at least part of a LIGA process). However, any way of making the inner housing 18 may be utilized. It should also be appreciated that the inner housing 18 may include one or more coatings as desired/required as well (e.g., an electroplated metal; a coating to improve the biocompatibility of the inner housing 18, to make the exposed surfaces of the inner housing 18 more hydrophilic, to reduce the potential for the inner housing 18 causing any bio-fouling, or any combination thereof). In one embodiment, a self assembled monolayer coating (e.g., poly-ethylene-glycol) is applied in any appropriate manner (e.g., liquid or vapor phase, with vapor phase being the preferred technique) to all exposed surfaces of the inner housing 18.

The outer housing 14 likewise is only schematically represented in FIGS. 1-2, and it may be of any appropriate shape/configuration, of any appropriate size, and formed from any material or combination of materials (e.g., polymethylmethacrylate (PMMA), titanium, and other implantable metals and plastics). Typically its outer contour will be adapted to match the inner contour of the housing or conduit in which it is at least partially disposed or otherwise mounted. The outer housing 14 also may be microfabricated into the desired/required shape (e.g., using at least part of a LIGA process). However, any way of making the outer housing 14 may be utilized. It should also be appreciated that the outer housing 14 may include one or more coatings as desired/required as well (e.g., an electroplated metal; a coating to improve the biocompatibility of the outer housing 14, to make the exposed surfaces of the outer housing 14 more hydrophilic, to reduce the potential for the outer housing 14 causing any bio-fouling, or any combination thereof). In one embodiment, a self assembled monolayer coating (e.g., poly-ethylene-glycol) is applied in any appropriate manner (e.g., liquid or vapor phase, with vapor phase being the preferred technique) to all exposed surfaces of the outer housing 14.

Figure 3B:
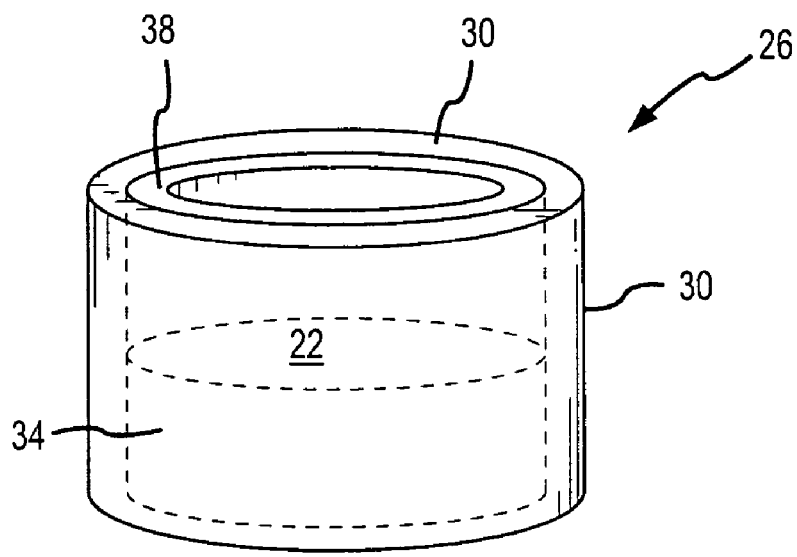
FIG. 3B is a perspective view of the flow assembly of FIG. 3A in an assembled condition.
Figure 3A:
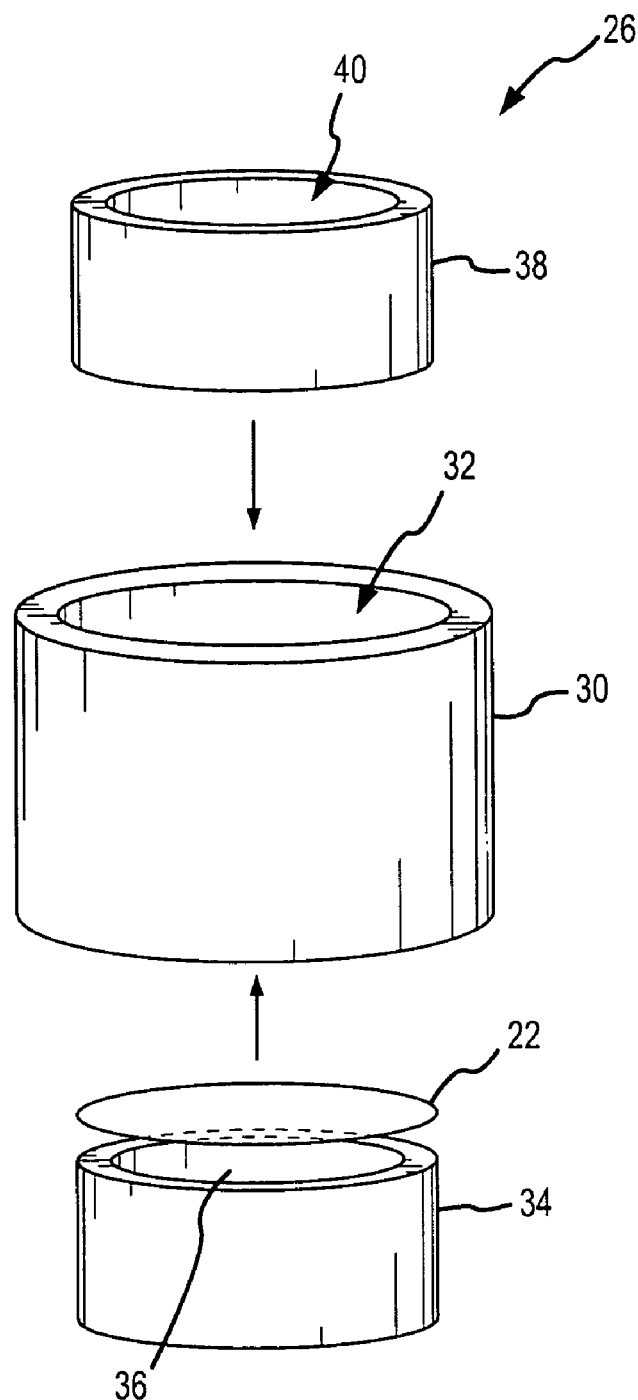
FIG. 3A is an exploded, perspective of another embodiment of a flow assembly that uses a MEMS flow module.

Another embodiment of a flow assembly is illustrated in FIGS. 3A-B (only schematic representations), and is identified by reference numeral 26. The flow assembly 26 may be used for any appropriate application (e.g., the flow assembly 26 may be disposed in a flow of any type, may be used to filter and/or control the flow of a fluid of any type, may be located in a conduit that fluidly interconnects multiple sources of any appropriate type (e.g., multiple fluid or pressure sources (including where one is the environment), such as a man-made reservoir, a biological reservoir, the environment, or any other appropriate source, or any combination thereof). The above-noted applications for the flow assembly 10 are equally applicable to the flow assembly 26. The types of coatings discussed above in relation to the flow assembly 10 may be used by the flow assembly 26 as well.

Components of the flow assembly 26 include an outer housing 30, a first inner housing 34, a second inner housing 38, and the MEMS flow module 22. The MEMS flow 22 and the inner housings 34, 38 are at least generally depicted within the outer housing 30 in FIG. 3B to show the relative positioning of these components in the assembled condition—not to convey that the outer housing 30 needs to be in the form of a transparent structure. All details of the MEMS flow module 22 and the inner housings 34, 38 are not necessarily illustrated in FIG. 3B.

The primary function of the outer housing 30, first inner housing 34, and second inner housing 38 is to provide structural integrity for the MEMS flow module 22 or to support the MEMS flow module 22, and further to protect the MEMS flow module 22. In this regard, the outer housing 30, first inner housing 34, and second inner housing 38 each will typically be in the form of a structure that is sufficiently rigid to protect the MEMS flow module 22 from being damaged by the forces that reasonably could be expected to be exerted on the flow assembly 26 during its assembly, as well as during use of the flow assembly 26 in the application for which it was designed.

The first inner housing 34 includes a hollow interior or a flow path 36 that extends through the first inner housing 34. Similarly, the second inner housing 38 includes a hollow interior or a flow path 40 that extends through the second inner housing 38. The first inner housing 34 and the second inner housing 40 are disposed in end-to-end relation, with the MEMS flow module 22 being disposed between adjacent ends of the first inner housing 34 and the second inner housing 38. As such, a flow progressing through the first flow path 36 to the second flow path 40, or vice versa, passes through the MEMS flow module 22.

Preferably, the MEMS flow module 22 is maintained in a fixed position relative to each inner housing 34, 38, and its perimeter does not protrude beyond the adjacent sidewalls of the inner housings 34, 38 in the assembled and joined condition. For instance, the MEMS flow module 22 may be bonded to at least one of, but more preferably both of, the first inner housing 34 (more specifically one end thereof) and the second inner housing 38 (more specifically one end thereof) to provide structural integrity for the MEMS flow module 22 (e.g., using cyanoacrylic esters, UV-curable epoxies, or other epoxies). Another option would be to fix the position the MEMS flow module 22 in the flow assembly 26 at least primarily by fixing the position of each of the inner housings 34, 38 relative to the outer housing 30 (i.e., the MEMS flow module 22 need not necessarily be bonded to either of the housings 34, 38). In one embodiment, an elastomeric material may be disposed between the MEMS flow module 22 and the first inner housing 34 to allow the first inner housing 34 with the MEMS flow module 22 disposed thereon to be pushed into the outer housing 30 (e.g., the elastomeric material is sufficiently "tacky" to at least temporarily retain the MEMS flow module 22 in position relative to the first inner housing 34 while being installed in the outer housing 30). The second inner housing 38 also may be pushed into the outer housing 30 (before, but more likely after, the first inner housing 34 is disposed in the outer housing 30) to "sandwich" the MEMS flow module 22 between the inner housings 34, 38 at a location that is within the outer housing 30 (i.e., such that the outer housing 30 is disposed about MEMS flow module 22). The MEMS flow module 22 would typically be contacted by both the first inner housing 34 and the second inner housing 38 when disposed within the outer housing 30. Fixing the position of each of the first inner housing 34 and the second inner housing 38 relative to the outer housing 30 will thereby in effect fix the position of the MEMS flow module 22 relative to the outer housing 30.

Both the first inner housing 34 and second inner housing 38 are at least partially disposed within the outer housing 30 (thereby encompassing the outer housing 30 being disposed about either or both housings 34, 38 along the entire length thereof, or only along a portion of the length thereof), again with the MEMS flow module 22 being located between the adjacent ends of the first inner housing 34 and the second inner housing 38. In this regard, the outer housing 30 includes a hollow interior 32 for receiving at least part of the first inner housing 34, at least part of the second inner housing 38, and the MEMS flow module 22 disposed therebetween, and possibly to provide other appropriate functionality (e.g., a flow path fluidly connected with the flow paths 36, 40 through the first and second inner housings 34, 38, respectively). The outer and inner sidewalls of the outer housing 30 may be cylindrical or of any other appropriate shape, as may be the outer and inner sidewalls of the inner housings 34, 38. Both the first inner housing 34 and the second inner housing 38 may be secured to the outer housing 30 in any appropriate manner, including in the manner discussed above in relation to the inner housing 18 and the outer housing 14 of the embodiment of FIGS. 1-2.

Each inner housing 34, 38 is likewise only schematically represented in FIGS. 3A-B, and each may be of any appropriate shape/configuration, of any appropriate size, and formed from any material or combination of materials in the same manner as the inner housing 18 of the embodiment of FIGS. 1-2. Typically the outer contour of both housings 34, 38 will be adapted to match the inner contour of the outer housing 30 in which they are at least partially disposed. In one embodiment, the illustrated cylindrical configuration for the inner housings 34, 38 is achieved by cutting an appropriate length from hypodermic needle stock. The inner housings 34, 38 each also may be microfabricated into the desired/required shape (e.g.,. using at least part of a LIGA process). However, any way of making the inner housings 34, 38 may be utilized. It should also be appreciated that the inner housings 34, 38 may include one or more coatings as desired/required in accordance with the foregoing.

The outer housing 30 is likewise only schematically represented in FIGS. 3A-B, and it may be of any appropriate shape/configuration, of any appropriate size, and formed from any material or combination of materials in the same manner as the outer housing 14 of the embodiment of FIGS. 1-2. Typically the outer contour of the outer housing 30 will be adapted to match the inner contour of the housing or conduit in which it is at least partially disposed or otherwise mounted. The outer housing 30 may be microfabricated into the desired/required shape (e.g., using at least part of a LIGA process). However, any way of making the outer housing 30 may be utilized. It should also be appreciated that the outer housing 30 may include one or more coatings as desired/required in accordance with the foregoing.

Figure 4A:
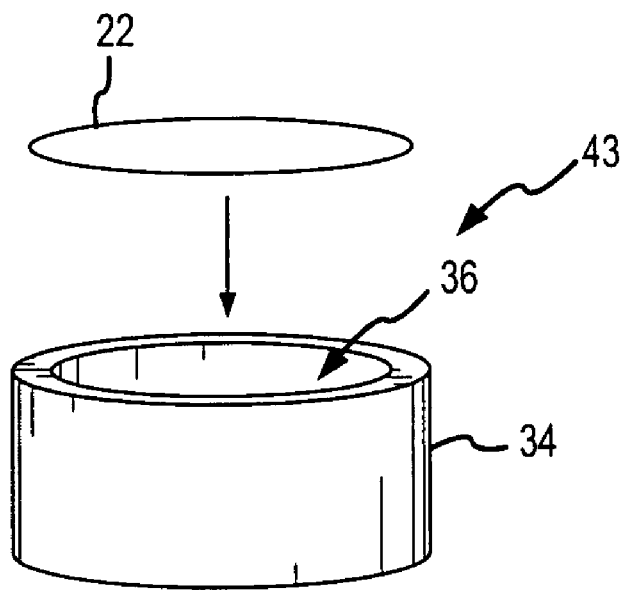
FIG. 4A is an exploded, perspective of another embodiment of a flow assembly that uses a MEMS flow module.
Figure 4B:
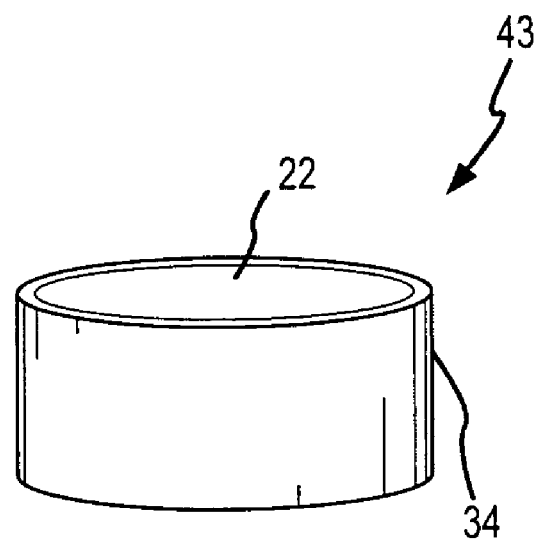
FIG. 4B is a perspective view of the flow assembly of FIG. 4A in an assembled condition.

Another embodiment of a flow assembly is illustrated in FIGS. 4A-B (only schematic representations), and is identified by reference numeral 43. The flow assembly 43 may be used for any appropriate application (e.g., the flow assembly 43 may be disposed in a flow of any type, may be used to filter a fluid of any type, may be located in a conduit that fluidly interconnects multiple sources of any appropriate type (e.g., between multiple fluid or pressure sources, such as-a man-made reservoir, a biological reservoir, the environment, or any other appropriate source, or any combination thereof). Components of the flow assembly 43 include the above-noted housing 34 and the MEMS flow module 22 from the embodiment of FIGS. 3A-B. In the case of the flow assembly 43, the MEMS flow module 22 is attached or bonded to one end of the housing 34 (e.g., using cyanoacrylic esters, UV-curable epoxies, or other epoxies).

The flow assembly 43 may be disposed within an outer housing in the manner of the embodiments of FIGS. 1-3B, or could be used "as is." The above-noted applications for the flow assembly 10 are equally applicable to the flow assembly 43. The types of coatings discussed above in relation to the flow assembly 10 may be used by the flow assembly 43 as well.

Figure 5A:
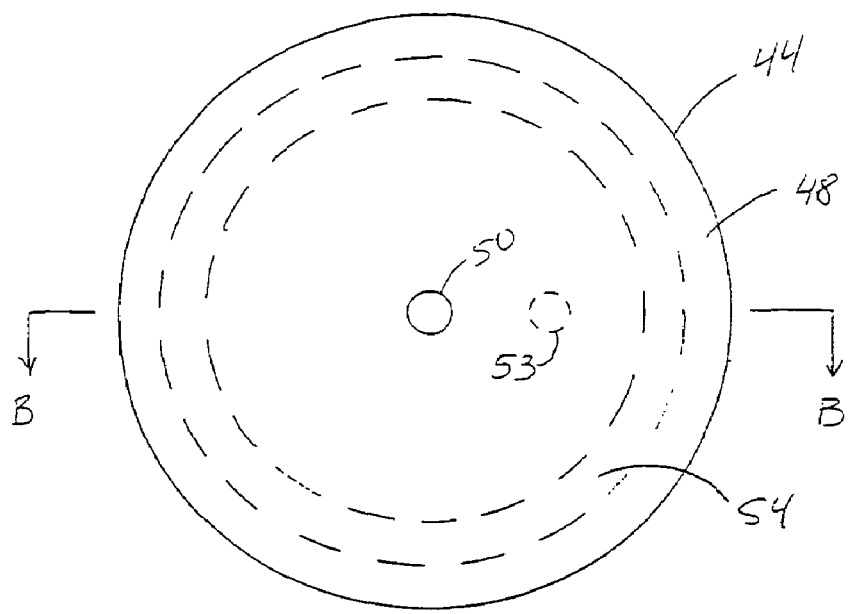
FIG. 5A is a schematic (top view) of one embodiment of a MEMS flow module.
Figure 5B:
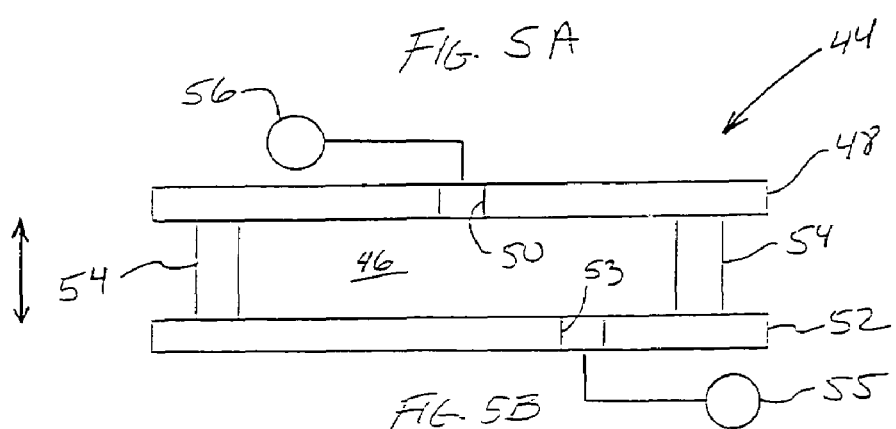
FIG. 5B is a cutaway, side view of the MEMS flow module of FIG. 5A, showing only the upper and lower plates and the interconnecting annular support.

The general construction of one embodiment of a MEMS flow module (a MEMS device) is illustrated in FIGS. 5A-B, is identified by reference numeral 44, and may provide both filtration and pressure or flow regulation functions, or either one individually. Generally, the MEMS flow module 44 of FIGS. 5A-B may be used in place of the MEMS flow module 22 discussed above in relation to the flow assemblies 10, 26, and 43 of FIGS. 1-4B. Although the MEMS flow module 44 is illustrated as having a circular configuration in plan view, any appropriate configuration may be utilized and in any appropriate size.

The MEMS flow module 44 of FIGS. 5A-B includes a lower plate 52, a vertically spaced upper plate 48, and at least one annular support 54. "Annular" means that the support(s) 54 extends 360 degrees about a reference axis to define a closed perimeter for the MEMS flow module 44. Any configuration may be used to define this annular extent for the annular support(s) 54 (e.g., square, rectangular, circular, oval). The annular support(s) 54 provides a certain amount of structural rigidity for the MEMS flow module 44 about its perimeter. The annular support(s) 54 also maintains the lower plate 52 and upper plate 48 in spaced relation such that the lower plate 52, upper plate 48, and the innermost annular support 54 collectively define an enclosed space 46 for receiving a fluid flow. Multiple, laterally spaced annular supports 54 (e.g., concentrically disposed) may be used as well. It should be appreciated that the terms "upper", "lower", and "lateral" are purely for definitional purposes, and do not require the MEMS flow module 44 to be used in any particular orientation.

The lower plate 52 includes at least one lower flow port 53, while the upper plate 48 includes at least one upper flow port 50. All lower flow ports 53 and all upper flow ports 50 are disposed inwardly of the innermost annular support 54. That is, the annular support(s) 54 also provides a seal in the radial or lateral dimension, thereby forcing the flow through the various upper flow ports 50 and/or lower flow ports 53. Providing multiple, radially or laterally spaced annular supports 54 further reduces the potential for any flow escaping from the enclosed space 46 other than through one or more upper flow ports 50 or one or more lower flow ports 53.

Each lower flow port 53 may be fluidly connected with a common first source 55 in any appropriate manner, while each upper flow port 50 may be fluidly connected with a common second source 56 in any appropriate manner. Typically the first source 55 will be at a higher pressure than the second source 56, although such may not be required in all instances. In any case, each source 55, 56 may be of any appropriate type (e.g., man-made, biological, the environment), may contain any appropriate type of fluid or combination of fluids, may be of any appropriate size, and may be of any appropriate configuration. In one embodiment, both sources 55 are man-made reservoirs. Another embodiment has one of the sources 55, 56 being a biological reservoir (e.g., an anterior chamber of a human eye; a cranial reservoir or chamber), with the other source 55, 56 being the environment or a man-made reservoir. For instance, the MEMS flow module 44 may be used by an implant to relieve intaocular or cranial pressure, may be used to deliver a drug or a combination of drugs to any source, or may be adapted for any appropriate application. In this regard, the MEMS flow module 44 may use the coatings discussed above in relation to the MEMS flow module 22.

A baffle, tuning element, or other movable flow control element (not shown) is disposed in the enclosed space 46 of the MEMS flow module 44, preferably in spaced relation to each of the lower plate 52 and the upper plate 48. Generally and as will be discussed in relation to the embodiments of FIGS. 6-13, this tuning element may provide both a filtering function and a pressure or flow regulation function. MEMS flow module 44 accommodates a flow of at least some type in either direction, as indicated by the double-headed arrow in FIG. 5B. The pressure or flow regulation function may be provided for a flow in one direction through the MEMS flow module 44 (e.g., from the first source 55 to the second source 56), while the filtration function may be provided for a flow in the opposite direction through the MEMS flow module 44 (e.g., from the second source 56 to the first source 55).

The lower plate 52 and the upper plate 48 are parallel to each other. The above-noted tuning element (at least the general lateral extent thereof) will also be disposed in parallel and preferably spaced relation to each of the lower plate 52 and upper plate 48 (e.g., FIGS. 6-13 to be discussed below). The MEMS flow module 44 may be fabricated by surface micromachining. In this regard, each of the lower plate 52, the upper plate 48, and the noted tuning element will be in the form of a film, typically having a thickness of no more than about 10 microns. In addition, the lower plate 52 and the upper plate 48 may be fabricated by surface micromachining so as to be separated by a distance of no more than about 20 microns. Although the flow module 44 may be fabricated by surface micromachining in various dimensions to suit the particular application in which it is being used, in one embodiment the volume of the enclosed space 46 is no more than about 0.002 $cm^3$ and the surface area encompassed by the perimeter of each of the lower plate 52 and the upper plate 48 is no more than about 1 $cm^2$.

The preferred fabrication technique for the MEMS flow module 44, and the variations thereof to be addressed below, is surface micromachining. Surface micromachining generally entails depositing alternate layers of structural material and sacrificial material using an appropriate substrate (e.g., a silicon wafer) which functions as the foundation for the resulting microstructure. Various patterning operations (collectively including masking, etching, and mask removal operations) may be executed on one or more of these layers before the next layer is deposited so as to define the desired microstructure. After the microstructure has been defined in this general manner, all or a portion of the various sacrificial layers are removed by exposing the microstructure and the various sacrificial layers to one or more etchants. This is commonly called "releasing" the microstructure from the substrate, typically to allow at least some degree of relative movement between the microstructure and the substrate. One particularly desirable surface micromachining technique is described in U.S. Pat. No. 6,082,208, that issued Jul. 4, 2000, that is entitled "Method For Fabricating Five-Level Microelectromechanical Structures and Microelectromechanical Transmission Formed," and the entire disclosure of which is incorporated by reference in its entirety herein (hereafter the '208 Patent).

The term "sacrificial layer or film" as used herein means any layer or portion thereof of any surface micromachined microstructure that is used to fabricate the microstructure, but which does not exist in the final configuration. Exemplary materials for the sacrificial layers described herein include undoped silicon dioxide or silicon oxide, and doped silicon dioxide or silicon oxide ("doped" indicating that additional elemental materials are added to the film during or after deposition). The term "structural layer or film" as used herein means any other layer or portion thereof of a surface micromachined microstructure other than a sacrificial layer and a substrate on which the microstructure is being fabricated. The "plates" and "tuning element" of the various MEMS flow modules to be described herein may be formed from such a structural layer or film. Exemplary materials for the structural layers described herein include doped or undoped polysilicon and doped or undoped silicon. Exemplary materials for the substrates described herein include silicon. The various layers described herein may be formed/deposited by techniques such as chemical vapor deposition (CVD) and including low-pressure CVD (LPCVD), atmospheric-pressure CVD (APCVD), and plasma-enhanced CVD (PECVD), thermal oxidation processes, and physical vapor deposition (PVD) and including evaporative PVD and sputtering PVD, as examples.

In more general terms, surface micromachining can be done with any suitable system of a substrate, sacrificial film(s) or layer(s) and structural film(s) or layer(s). Many substrate materials may be used in surface micromachining operations, although the tendency is to use silicon wafers because of their ubiquitous presence and availability. The substrate is essentially a foundation on which the microstructures are fabricated. This foundation material must be stable to the processes that are being used to define the microstructure(s) and cannot adversely affect the processing of the sacrificial/structural films that are being used to define the microstructure(s). With regard to the sacrificial and structural films, the primary differentiating factor is a selectivity difference between the sacrificial and structural films to the desired/required release etchant(s). This selectivity ratio may be on the order of about 10:1, and is more preferably several hundred to one or much greater, with an infinite selectivity ratio being most preferred. Examples of such a sacrificial film/structural film system include: various silicon oxides/various forms of silicon; poly germanium/poly germanium-silicon; various polymeric films/various metal films (e.g., photoresist/aluminum); various metals/various metals (e.g., aluminum/nickel), polysilicon/silicon carbide; silicone dioxide/polysilicon (i.e., using a different release etchant like potassium hydroxide, for example). Examples of release etchants for silicon dioxide and silicon oxide sacrificial materials are typically hydrofluoric (HF) acid based (e.g., undiluted or concentrated HF acid, which is actually 49 wt % HF acid and 51 wt % water; concentrated HF acid with water; buffered HF acid (HF acid and ammonium fluoride)).

The microfabrication technology described in the above-noted '208 Patent uses a plurality of alternating structural layers (e.g., polysilicon and therefore referred to as "P" layers herein) and sacrificial layers (e.g., silicon dioxide, and therefore referred to as "S" layers herein). The nomenclature that is commonly used to describe the various layers in the microfabrication technology described in the above-noted '208 Patent will also be used herein.

Figure 5C:
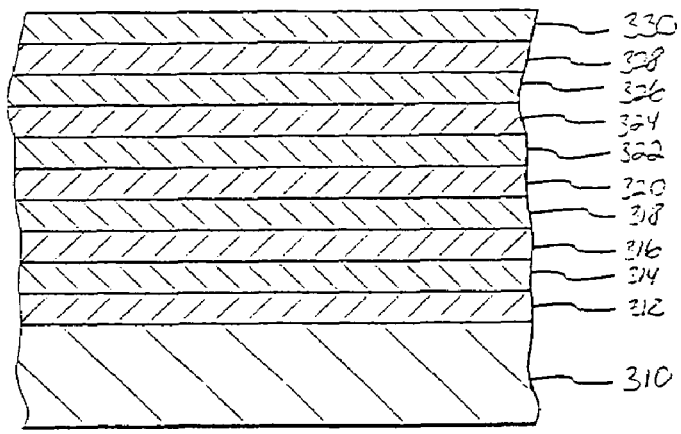
FIG. 5C is a cross-sectional view of the various layers that may be used by one embodiment of a surface micromachining process to fabricate to the MEMS flow control modules described herein.

FIG. 5C generally illustrates one embodiment of layers on a substrate 310 that is appropriate for surface micromachining and in accordance with the nomenclature commonly associated with the '208 Patent. Progressing away from the substrate 310, the various layers are: a dielectric layer 312 (there may be an intermediate oxide layer between the dielectric layer 312 and the substrate 310 as well, which is not shown); a $P_0$ layer 314; an $S_1$ layer 316; a $P_1$ layer 318; an $S_2$ layer 320; a $P_2$ layer 322; an $S_3$ layer 324; a $P_3$ layer 326; an $S_4$ layer 328; and a $P_4$ layer 330. In some cases, the $S_2$ layer 320 may be removed before the etch release such that the $P_2$ layer 322 is deposited directly on the $P_1$ layer 318. It should also be appreciated that one or more other layers may be deposited on the $P_4$ layer 330 after the formation thereof and prior to the etch release, where the entirety of the $S_1$ layer 316, $S_2$ layer 320, $S_3$ layer 324, and $S_4$ layer 328 may be removed (although portions of one or more of these layers may be retained for one or more purposes if properly encased so as to be protected from the release etchant). It should also be appreciated that adjacent structural layers may be structurally interconnected by forming cuts or apertures through the entire thickness of a particular sacrificial layer before depositing the next structural layer. In this case, the structural material will not only be deposited on the upper surface of the particular sacrificial layer, but will be deposited in these cuts or apertures as well (and will thereby interconnect a pair of adjacent, spaced, structural layers).

Various embodiments in accordance with the above-noted parameters of the MEMS flow module 44 are illustrated in FIGS. 6-13. Each of these embodiments illustrates a baffle, tuning element, or other flow control element of the above-noted type. Unless otherwise noted, the discussion on the MEMS flow module 44 and the various individual components thereof is equally applicable to these designs (e.g., each such MEMS flow module may use the coatings discussed above in relation to the MEMS flow module 22). Although the preferred design is for each of these MEMS flow modules to include an upper plate and at least one annular support, such may not be required for all applications for which these MEMS flow modules are appropriate. Moreover, the tuning element in each of these embodiments is preferably always in spaced relation to the underlying lower plate, which has at least one lower flow port. However, each of these embodiments also could be designed so that the tuning element is disposed directly on the lower plate until at least a certain pressure is exerted thereon, after which it would move into spaced relation with the lower plate to define a flow channel to accommodate a change in direction of the flow within the MEMS flow module. Each of these MEMS flow modules may be designed for a laminar flow therethrough, although each such MEMS flow module may be applicable for a turbulent flow therethrough as well.

Figure 6:
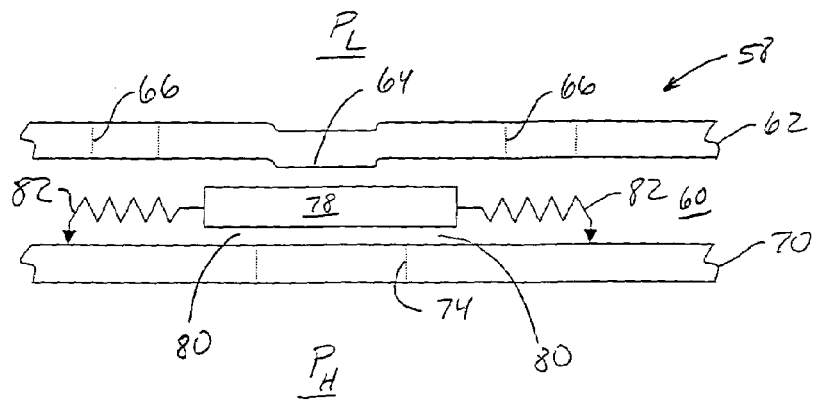

One embodiment of a MEMS flow module is illustrated in FIG. 6 and identified by reference numeral 58. The MEMS flow module 58 includes an upper plate 62 (e.g., fabricated in $P_4$ layer 330), a lower plate 70 (e.g., fabricated in $P_2$ layer 322 or a combined $P_2$ layer 322 and $P_1$ layer 318) that is parallel with the upper plate 62, and at least one annular support 54 of the type used in the embodiment of FIGS. 5A-B (not shown in FIG. 6). The annular support(s) 54 provides the same function as in the case of the embodiment of FIGS. 5A-B, including maintaining the upper plate 62 and lower plate 70 in spaced relation such that the upper plate 62, lower plate 70, and the innermost annular support 54 collectively define an enclosed space 60. The upper plate 62 includes a plurality of upper flow ports 66, while the lower flow plate 70 includes at least one lower flow port 74. The flow ports 66, 70 may be of any appropriate configuration and/or size. All upper flow ports 66 and all lower flow ports 74 are disposed inwardly of the innermost annular support 54. That is, each annular support(s) 54 also provides a seal in the radial or lateral dimension, thereby forcing the flow through the various upper flow ports 66 and/or lower flow port(s) 74. Providing multiple, radially or laterally spaced annular supports 54 further reduces the potential for any flow escaping from the enclosed space 60 other than through one or more upper flow ports 66 or one or more lower flow ports 74.

At least one baffle, tuning element or other flow control element 78 (e.g., fabricated in $P_3$ layer 326) is disposed in the enclosed space 60 in spaced and parallel relation to each of the upper plate 62 and lower plate 70, and may be of any appropriate shape in plan view (looking down on the tuning element 78 in the view presented in FIGS. 6). The tuning element 78 is supported above the lower plate 70 by a plurality of springs 82 of any appropriate size and configuration (only schematically shown). The springs 82 could be configured to actually bias the tuning element 78 into contact with the lower plate 70 until a certain differential pressure exists across the MEMS flow module 58, at which time the tuning element 78 would then move away from the lower plate 70 (not shown). The main requirement of the springs 82 is that they allow the tuning element 78 to move to provide a desired pressure or flow regulation function in the manner addressed in more detail below. Generally, the tuning element 78 is able to move relative to the lower plate 70 by a bending or some other deformation (typically elastic) of the various springs 82 and in response to a change in the pressure being exerted by a flow entering the MEMS flow module 58 through its corresponding lower flow port(s) 74 on the side of the tuning element 78 that faces the lower plate 70. In this regard, the tuning element 78 may be characterized as a rigid structure, in that a flow into the MEMS flow module 58 will deform its corresponding springs 82 before deforming the tuning element 78.

The tuning element 78 is disposed above at least one lower flow port 74 (e.g., in overlying, but preferably spaced relation). If the tuning element 78 is disposed above multiple lower flow ports 74, preferably these lower flow ports 74 would be symmetrically positioned such that a flow entering the enclosed space 60 through such multiple lower flow ports 74 would exert a force on the tuning element 78 in a manner that would allow the tuning element 78 to at least substantially maintain its orientation during any movement of the tuning element 78 in providing the desired pressure regulation function. In any case, the existence of the tuning element 78 within the enclosed space 60 means that no flow proceeds through the MEMS flow module 58 along a purely linear path. That is, the tuning element 78 induces flow along a non-linear path within the enclosed space 60 by inducing at least one change in direction of the flow before exiting the MEMS flow module 58. In the illustrated embodiment, the flow is required to reach the perimeter of the tuning element 78 before it can again flow in the direction of the upper plate 62. In this regard, it is believed to be desirable to position one, and more preferably a plurality of, upper flow ports 66 at or slightly beyond the perimeter of the tuning element 78 (and positioned about the tuning element 78 at reasonable intervals) to reduce the overall length of the flow path through the MEMS flow module 58. A purely linear flow path (geometrically) through the MEMS flow module 58 does not exist absent some type of failure, since the tuning element 78 redirects flow entering the MEMS flow module 58 through the lower flow port(s) 74.

Any flow entering the enclosed space 60 through any lower flow port 74 must pass through a flow channel 80, which is the gap between the corresponding tuning element 78 and the lower plate 70. This flow channel 80 preferably exists at all times. Stated another way, the MEMS flow module 58 preferably is not designed for the tuning element 78 to ever be disposed against the lower plate 70, which would at least in effect terminate a flow into the enclosed space 60 through a lower flow port 74 being occluded by the tuning element 78. This "constantly open" flow channel 80 is beneficial in at least number of respects. One is that a configuration where the tuning element 78 is always maintained in spaced relation to the lower plate 70 is more readily fabricated by surface micromachining. Another relates to the case where the MEMS flow module 58 is used to relieve intraocular pressure in an eye (e.g., by being incorporated into an eye implant). In this case, the lower plate 70 of the MEMS flow module 58 would be on the "patient side," and the upper plate 62 would be on the "environment" side (e.g., the flow of aqueous humor out of the anterior chamber of the patient's eye through the MEMS flow module 58 in this case would be through one or more lower flow ports 74, into the enclosed space 60, and out one or more upper flow ports 66). Having the flow channel 80 exist at all times (such that is always has a volume greater than zero) is believed to at least generally mimic the flow of aqueous humor out of the anterior chamber of a patient's eye through the eye's canal of Schlemm. However and as noted above, the MEMS flow module 58 could be designed so that the tuning element 78 is disposed directly on the lower plate 70 until at least a certain pressure is exerted thereon (e.g., a pressure "set point"), after which it would move into spaced relation with the lower plate 70 to define the flow channel 80.

Typically the MEMS flow module 58 will be used in an application where a high pressure source PH (e.g., the anterior chamber of a patient's eye) fluidly connects with the enclosed space 60 through one or more lower flow ports 74, while a low pressure source $P_L$ (e.g., the environment) fluidly connects with the enclosed space 60 through one or more upper flow ports 66. A change in the pressure from the high pressure source $P_H$ may cause the tuning element 78 to move relative to the lower plate 70, which thereby changes the size of the flow channel 80. Preferably, a very small change in this pressure will allow for greater than a linear change in the flow rate out of the MEMS flow module 58 through the upper flow port(s) 66. For instance, a small increase in the pressure of the high pressure source $P_H$ may increase the height of the flow channel 80 (by the springs 82 allowing the tuning element 78 to move further away from the lower plate 70) to provide more than a linear increase in the flow rate through the flow channel 80, and thereby through the MEMS flow module 58. That is, there is a non-linear relationship between the flow rate exiting the MEMS flow module 58 and the pressure being exerted on the tuning element 78 by a flow entering the MEMS flow module 58 from the high pressure source $P_H$. The flow rate through the flow channel 80 should be a function of at least the cube of the height of the flow channel 80 (in the case of laminar flow, which is typically encountered at these dimensions and flow rates). Therefore, even a small change in the height of the flow channel 80 (e.g., due to even a small change in the pressure acting on the tuning element 78 from the high pressure source $P_H$) will cause at least a cubic change in the flow rate through the flow channel 80.

Consider the case where the MEMS flow module 58 is used in an implant to regulate the pressure in the anterior chamber of a patient's eye that is diseased, and where it is desired to maintain the pressure within the anterior chamber of this eye at about 5 mm of HG. The MEMS flow module 58 may be configured such that it will adjust the flow rate out of the anterior chamber and through the MEMS flow module 58 such that the maximum pressure within the anterior chamber of the patient's eye should be no more than about 7-8 mm of HG (throughout the range for which the MEMS flow module 58 is designed). Stated another way, the MEMS flow module 58 allows for maintaining at least a substantially constant pressure in the anterior chamber of the patient's eye (the high pressure source $P_H$ in this instance), at least for a reasonably anticipated range of pressures within the anterior chamber of the patient's eye. In order to account for unanticipated increases in pressure in the high pressure source $P_H$, the upper plate 62 includes at least one overpressure stop 64 for each tuning element 78 to limit the maximum spacing between the tuning element 78 and the lower plate 70. This then provides a limit on the maximum height of the flow channel 80, and thereby the maximum flow rate through the filter channel 80 for a certain pressure. That is, at least one overpressure stop 64 exists on the surface of the upper plate 62 that faces the lower plate 70, in vertical alignment with its corresponding tuning element 78. Each overpressure stop 64 may be of any appropriate size and/or shape (e.g., in the form of a post).

The tuning element 78 provides a pressure or flow regulation function in the above-noted manner. It also provides a filtering function. One could say the MEMS flow module 58 provides a pressure or flow regulation function for a flow into the enclosed space 60 through one or more lower flow ports 74 and in the direction of the low pressure source $P_L$, and a filtering function for a flow into the enclosed space 60 through one or more upper flow ports 66 and in the direction of the high pressure source $P_H$. Generally, since the height of the flow channel 80 is preferably always greater than zero, this flow channel 80 also functions as a filter trap gap for any "flow" entering the enclosed space 60 through one or more of the upper flow ports 66 that is attempting to proceed toward the high pressure source $P_H$. Any constituent in this "flow" having an effective diameter that is larger than the height of the flow channel 80 should be filtered out of this "flow", and should be unable to pass through the flow channel 80 and out of the enclosed space 60 through any lower filter port 74. That is, the size of the flow channel 80 at the perimeter of the tuning element 78 should prohibit constituents of larger than a certain size from entering the flow channel 80 and proceeding out of the MEMS flow module 58 through the lower flow port 74. In the case where the MEMS flow module 58 is used in an eye implant to regulate intraocular pressure, the maximum height of the flow channel 80 is about 0.5 micron based upon the overpressure stop 64, although the maximum height of the flow channel 80 for the reasonably expected differential pressures to which the tuning element 78 will be exposed for this application is about 0.4 micron. As such, it is unlikely that undesired bacteria should be able to pass through the flow channel 80 and out of the enclosed space 60 through a lower flow port 74 and into the anterior chamber of the patient's eye for the reasonably expected pressures within the anterior chamber of the patient's eye for which the MEMS flow module 58 is designed.

There are a number of features and/or relationships that contribute to the pressure or flow regulation function of the MEMS flow module 58, and that warrant a summarization. First is that the MEMS flow module 58 is a passive device—no external signal of any type need be used to move the tuning element 78 relative to the lower plate 70 to provide its pressure or flow regulation function. Instead, the position of the tuning element 78 relative to the lower plate 70 is dependent upon the pressure being exerted on the lower plate 70 by a flow entering the MEMS flow module 58 through the lower flow port(s) 74, and the flow rate out of the MEMS flow module 58 is in turn dependent upon the position of the tuning element 78 relative to the lower plate 70 (the vertical spacing therebetween, and thereby the size of the flow channel 80). The tuning element 78 is aligned with at least one lower flow port 74 for receiving a fluid from the high pressure source $P_H$. That is, the tuning element 78 is positioned such that a flow proceeding along the direction in which it is initially introduced into the enclosed space 60 of the MEMS flow module 58 will contact the tuning element 78 (e.g., the streamlines of this flow immediately before proceeding through the lower flow port 74 will intersect the tuning element 78). Further in this regard, the tuning element 78 is positioned such that this flow acts orthogonally on the tuning element 78. Stated another way, the force exerted on the tuning element 78 from any flow entering the MEMS flow module 58 from the high pressure source $P_H$ exerts a normal force on the tuning element 78 (e.g., the streamlines of the flow just prior to flowing through the corresponding lower flow port 74 will be perpendicular to the surface of the tuning element 78 that is aligned with this flow).

The position of the tuning element 78 within the enclosed space 60 of the MEMS flow module 58 is dependent upon the pressure being exerted on the tuning element 78 by a flow entering the MEMS flow module 58 from the lower flow port(s) 74—that is from the high pressure source $P_H$. At least a certain increase in this pressure will move the tuning element 78 further away from the lower plate 70 (increasing the size of the flow channel 80), while subsequent decreases in this pressure will move the tuning element 78 closer to the lower plate 70 (reducing the size of the flow channel 80). This movement of the tuning element 78 is subject to a number of characterizations. One is that the orientation of the tuning element 78 relative to other components of the MEMS flow module 58 is at least substantially maintained during this movement. Another is that at least the general extent of the upper surface of the tuning element 78 is maintained in parallel relation with the lower plate 70 during this movement. Another is that the tuning element 78 moves only at least substantially axially within the MEMS flow module 58 (e.g., along an axis that is collinear or parallel with the direction of the flow (e.g., its streamlines) entering the MEMS flow module 58 through the lower flow port(s) 74). Another is that the distance between the tuning element 78 and the lower plate 70 changes by at least substantially the same amount across the entirety of the surface of the tuning element 78 that faces the upper surface of the lower plate 70. Yet another is that the cross-sectional area of the flow channel 80 (the space between the tuning element 78 and the lower plate 70) changes at least substantially proportionally in the lateral dimension or along the length of the flow channel 80.

Regardless of the vertical position of the tuning element 78 within the MEMS flow module 58, the tuning element 78 redirects a flow entering the MEMS flow module 58 through the lower flow port(s) 74 before exiting the MEMS flow module 58 through the upper flow ports 66. The pressure of a flow from the high pressure source $P_H$ acts orthogonally on the tuning element 78, and then is redirected (at least generally 90 degrees in the illustrated embodiment) through the flow channel 80 (the space between the tuning element 78 and the lower plate 70. That is, a flow from the high pressure source $P_H$ must flow laterally along a flow channel 80 a certain distance before reaching the perimeter of the tuning element 78. Stated another way, a primary component of the direction of this flow through the flow channel 80 is toward the annular support(s) 54 versus toward the upper plate 62.

Once a flow from the high pressure source $P_H$ reaches the perimeter of the tuning element 78, it will then undergo another change in direction to flow toward the upper plate 62 and out of the MEMS flow module 58 through one or more of the upper flow ports 66. Preferably, at least a portion of the flow is able to proceed along an axial path (at least generally parallel to the direction of the flow as it originally entered the enclosed space 60 through the lower flow port(s) 74) from the perimeter of the tuning element 78 to an upper flow port 66 in the upper plate 62. The actual flow rate out of the upper flow port(s) 66 again is dependent upon the position of the tuning element 78 relative to the lower plate 70. The flow rate out of the MEMS flow module 58 will increase as the spacing between the tuning element 78 and the lower plate 70 increases, and will decrease as the spacing between the tuning element 78 and the lower plate 70 decreases.

The MEMS flow modules of FIGS. 7-13 use the same basic operational fundamentals as the MEMS flow module 58 of FIG. 6, and such will not be repeated in relation to each of these designs. Specifically, the discussion of the tuning element 78 of FIG. 6 is equally applicable to the tuning elements in the MEMS flow modules of FIGS. 7-13. That is, the baffle or tuning element of the MEMS flow modules of FIGS. 7-13 are each subject to the characterizations of the tuning element 78 of FIG. 6, including in relation to all aspects thereof to its movement for providing a pressure or flow regulation function. Only those additional attributes or those that differ in at least some respect will be addressed.

Figure 7A:
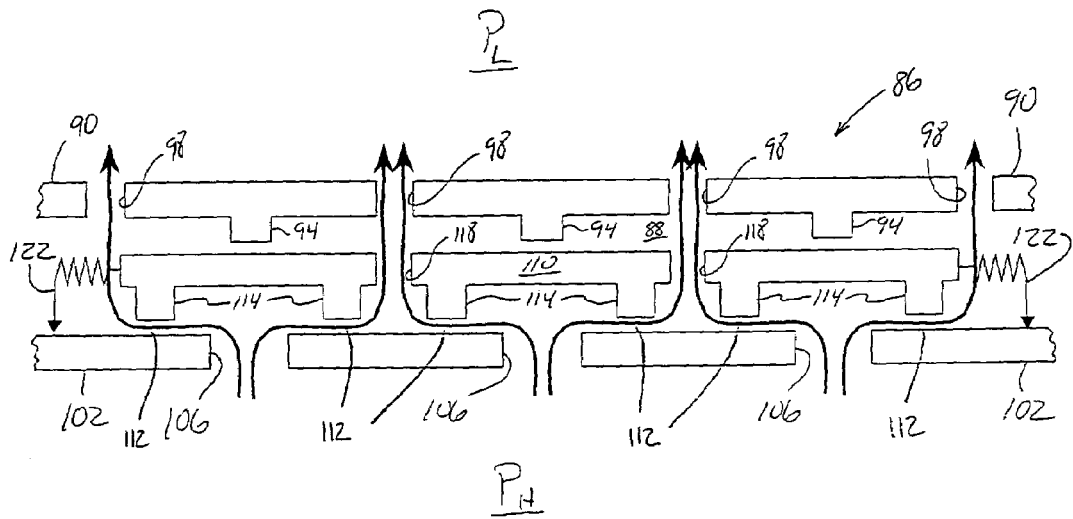
Figure 7B:
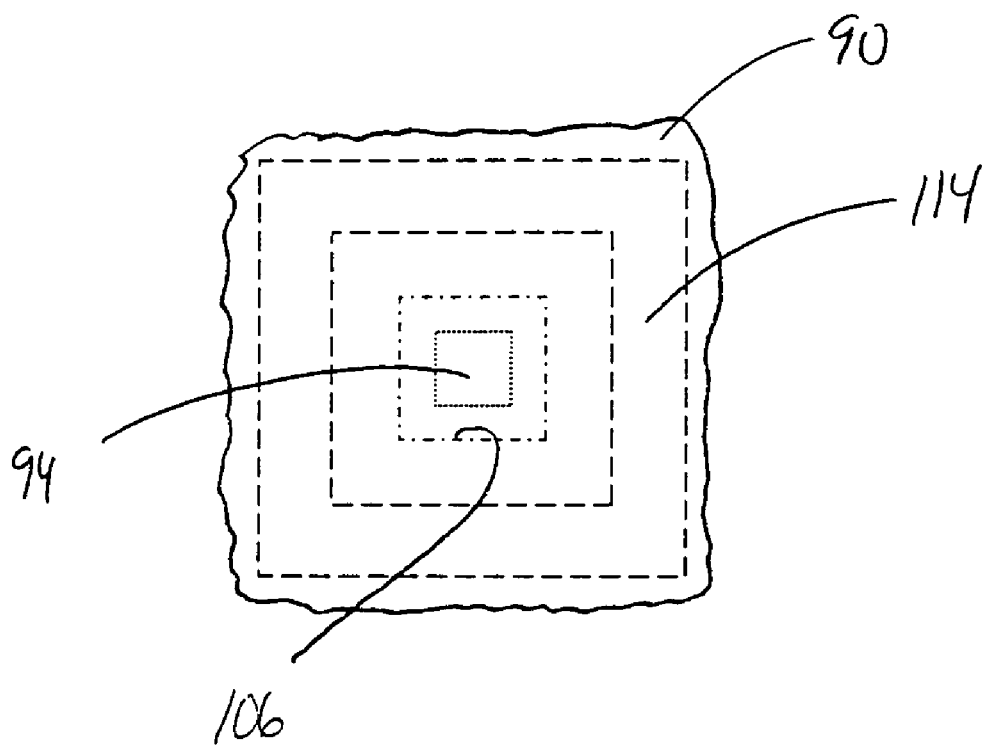

Another embodiment of a MEMS flow module is illustrated in FIGS. 7A-B and identified by reference numeral 86. The MEMS flow module 86 includes an upper plate 90 (e.g., fabricated in $P_4$ layer 330), a lower plate 102 (e.g., fabricated in $P_2$ layer 322 or a combined $P_2$ layer 322 and $P_1$ layer 318) that is parallel with the upper plate 90, and at least one annular support 54 of the type used in the embodiment of FIGS. 5A-B (not shown in FIG. 7A). The annular support(s) 54 maintains the upper plate 90 and lower plate 102 in spaced relation such that the upper plate 90, lower plate 102, and the innermost annular support 54 collectively define an enclosed space 88. The upper plate 90 includes a plurality of upper flow ports 98, while the lower flow plate 102 includes a plurality of lower flow ports 106. The flow ports 98, 106 may be of any appropriate size and/or shape. All upper flow ports 98 and all lower flow ports 106 are disposed inwardly of the innermost annular support 54. That is, each annular support(s) 54 also provides a seal in the radial or lateral dimension, thereby forcing the flow through the various upper flow ports 98 and/or lower flow ports 106. Providing multiple, radially or laterally spaced annular supports 54 would further reduce the potential for any flow escaping from the enclosed space 88 other than through one or more upper flow ports 98 or one or more lower flow ports 106.

At least one baffle, tuning element, or other flow control element 110 (e.g., fabricated in $P_3$ layer 326) is disposed in the enclosed space 88 in spaced and parallel relation to each of the upper plate 90 and lower plate 102 (only one shown), and may be of any appropriate shape in plan view (looking down on the tuning element 110 in the view presented in FIG. 7A). The tuning element 110 is supported above the lower plate 102 by a plurality of springs 122 of any appropriate size and configuration (only schematically shown). The main requirement of the springs 122 is that they allow the tuning element 110 to move to provide a desired pressure or flow regulation function in the manner discussed above in relation to the embodiment of FIG. 6. Generally, the tuning element 110 is able to move relative to the lower plate 102 by a bending or some other deformation (typically elastic) of the various springs 122 and in response to a change in the pressure being exerted by a flow entering the MEMS flow module 86 through its corresponding lower flow port(s) 106 on the side of the tuning element 110 that faces the lower plate 70. In this regard, the tuning element 110 may be characterized as a rigid structure, in that a flow into the MEMS flow module 86 will deform its corresponding springs 122 before deforming the tuning element 110.

The movement of the tuning element 110 away from and toward the lower plate 102 to provide a pressure or flow regulation function again is one where the tuning element 110 at least substantially maintains its orientation relative to the lower plate 102. The upper plate 90 includes a plurality of overpressure stops 94 for each tuning element 110 to again limit the maximum travel of the tuning element 110 away from the lower plate 102 (to provide a maximum height of a flow channel 112—that is, the space between the tuning element 110 and the lower plate 102). Each such overpressure stop 94 may be of any appropriate size and/or shape (e.g., a post).

The tuning element 110 is disposed above a plurality of lower flow ports 106 (e.g., in overlying, but spaced relation). Preferably, this plurality of lower flow ports 106 are symmetrically positioned such that a flow entering the enclosed space 88 through such multiple lower flow ports 106 exerts a force on the tuning element 110 in a manner that allows the tuning element 110 to at least substantially maintain its orientation relative to the upper plate 90 and the lower plate 102. In any case, the existence of the tuning element 110 within the enclosed space 88 means that no flow through the MEMS flow module 86 is along a purely linear path. That is, the tuning element 110 induces flow along a non-linear path (geometrically) within the enclosed space 88 by inducing at least one change in direction of the flow before exiting the MEMS flow module 86. In this regard, the tuning element 110 includes a plurality of tuning element flow ports 118. However, no tuning element flow port 118 is vertically aligned with any lower flow port 106. As such, flow entering the enclosed space 88 through a particular lower flow port 106 must flow in the radial or lateral dimension through a flow channel 112 before reaching a tuning element flow port 118 of its corresponding tuning element 110 or the perimeter of the tuning element 110. In the illustrated embodiment, an upper flow port 98 is vertically aligned with each tuning element flow port 118 and a number of upper flow ports 98 are disposed at or slightly beyond a location in the lateral dimension corresponding with the perimeter of the tuning element 110 to reduce the overall length of the flow path through the MEMS flow module 86. A purely linear flow path (geometrically) through the MEMS flow module 86 does not exist absent some type of failure, since the tuning element 110 redirects flow entering the MEMS flow module 86 through the lower flow port(s) 106.

Any flow entering the enclosed space 88 through any lower flow port 106 must pass through a flow channel 112, which is the gap between the corresponding tuning element 110 and the lower plate 102. This flow channel 112 preferably exists at all times in the same manner as the flow channel 80 in the FIG. 6 embodiment discussed above. However, the tuning element 110 could be designed to be in contact with the lower plate 102 until a certain pressure "set point" is reached, after which the tuning element 110 would move into spaced relation with the lower plate 102. In any case, flow entering the MEMS flow module 86 through the lower flow ports 106 is redirected by the tuning element 110 into the flow channel 112. Thereafter, the flow undergoes another change in direction to flow through one or more of the tuning element flow ports 118 or around the perimeter of the tuning element 110 in order to exit the MEMS flow module 86 through one or more of the upper flow ports 98.

The tuning element 110 also includes an annular filter wall 114 for each lower flow port 106. "Annular" simply means that the filter wall 114 extends a full 360 degrees about a certain reference axis to provide a closed perimeter (see FIG. 7B). Any configuration that provides this annular extent may be utilized (e.g., circular, square, rectangular, triangular). The filter walls 114 are disposed on a surface of the tuning element 110 that faces the lower plate 102. The area encompassed by projecting each filter wall 114 onto the lower plate 102 encompasses the corresponding lower flow port 106 (see FIG. 7B). The gap between a particular filter wall 114 and the underlying structure (e.g., the lower plate 102) filters a flow into the MEMS flow module 86 that attempts to proceed through this gap in order to exit the MEMS flow module 86 through one or more lower flow ports 106. Any configuration of a filter wall 114 that provides a restricted flow into its corresponding lower flow port 106 may be utilized (e.g., FIGS. 11B-C).

Figure 8:
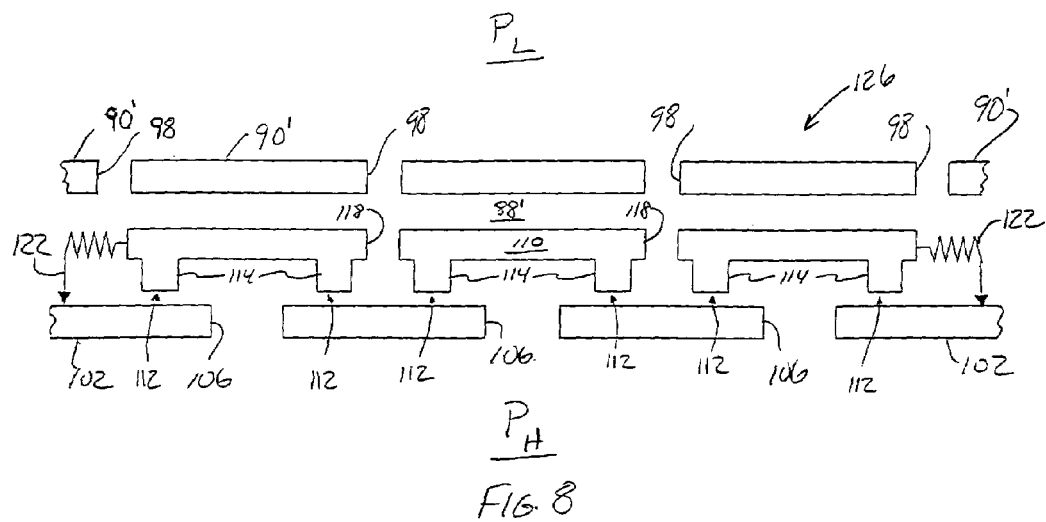

Another embodiment of a MEMS flow module is illustrated in FIG. 8 and identified by reference numeral 126. The only difference between the MEMS flow module 126 of FIG. 8 and the MEMS flow module 86 of FIGS. 7A-B is that there are no overpressure stops on the upper plate 90' in the case of the MEMS flow module 126 (therefore, a "single prime" designation is used in relation to upper plate 90' in FIG. 8). Therefore, the travel of the tuning element 110 away from the lower plate 102 will be limited by engagement with the upper plate 90' in the case of the MEMS flow module 126. Since there is a change in the inner volume within the MEMS flow module 126 by the removal of the overpressure stops 94, the enclosed space 88' also uses the "single prime" designation.

Figure 9:
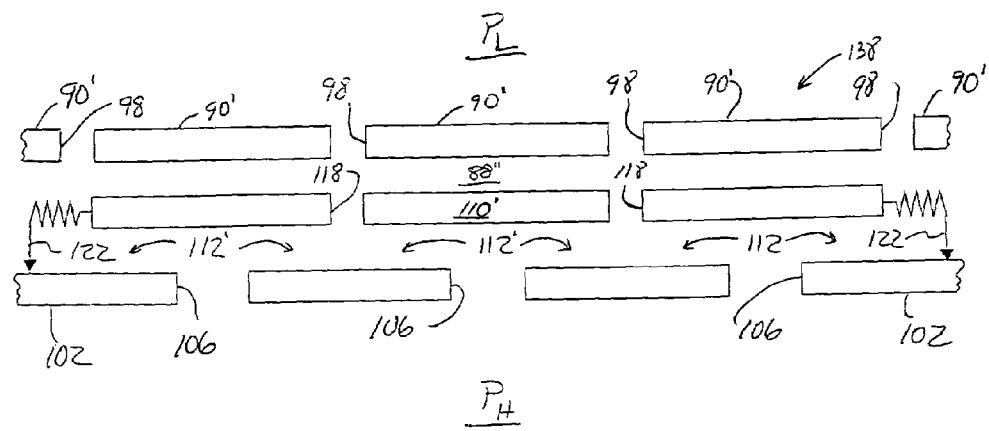

Another embodiment of a MEMS flow module is illustrated in FIG. 9 and identified by reference numeral 138. The only difference between the MEMS flow module 138 of FIG. 9 and the MEMS flow module 126 of FIG. 8 is that there are no filter walls 114 on the baffle, tuning element, or other flow control element 110' in the case of the MEMS flow module 138 (therefore, a "single prime" designation is used in relation to tuning element 110' in FIG. 9). Since there is a change in the inner volume within the MEMS flow module 136 from that of the MEMS flow module 126, the enclosed space 88" in FIG. 9 also uses a "double prime" designation.

Another embodiment of a MEMS flow module is illustrated in FIG. 10 and identified by reference numeral 168. This MEMS flow module 168 is similar to that discussed above in relation to FIG. 6. However, there are a number of differences between the MEMS flow module 168 of FIG. 10 and the MEMS flow module 58 of FIG. 6. One is that the baffle, tuning element, or other flow control element 78' is larger in the lateral dimension and is disposed over multiple lower flow ports 74 (therefore, a "single prime" designation is used in relation to tuning element 78' in FIG. 10). Since the flow channel 80' has a larger extent in the lateral dimension as well in the case of the MEMS flow module 168 of FIG. 10, it is identified using a "single prime" designation. Yet another distinction is that the tuning element 78' includes a plurality of tuning element flow ports 170. These tuning port flow ports 170 could be vertically aligned with an upper flow port 66 in the manner of the embodiments of FIGS. 7A-B, 8 and 9, but are offset from the lower flow ports 74. The arrows in FIG. 10 illustrate the direction of the force being exerted on the tuning element 78' by a flow entering the MEMS flow module 168 through the lower flow ports 74.

Figure 11A:
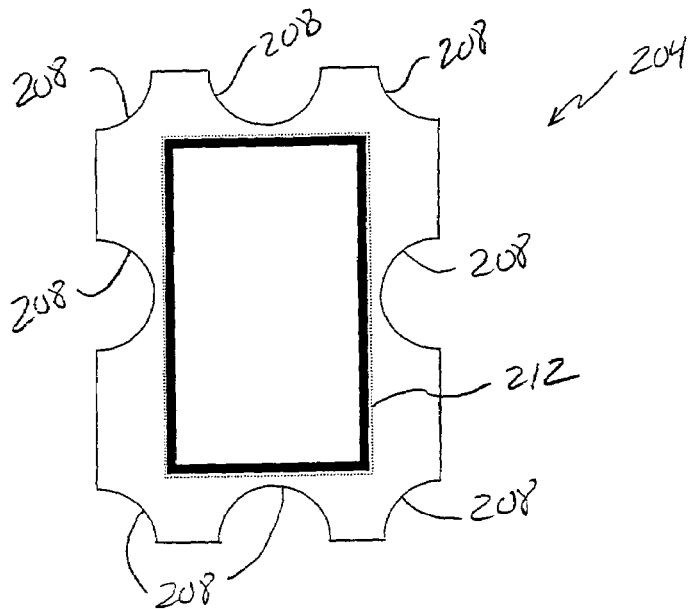
FIG. 11A is a top, plan view of a tuning element unit cell.
Figure 12:
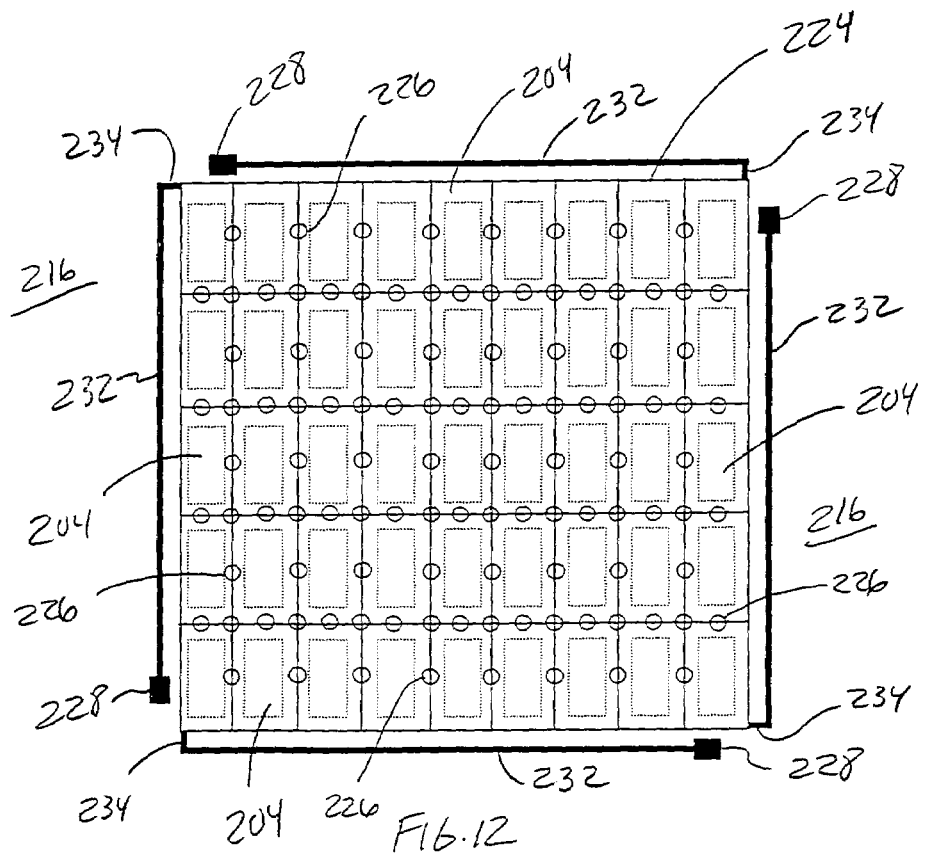
FIG. 12 is a top, plan view of a MEMS tuning element having a plurality of tuning element unit cells of the configuration of FIG. 11A.

FIG. 11A illustrates what may be characterized as a single baffle or tuning element unit cell 204 that may define a baffle or single tuning element (FIGS. 11B-C) or that may be "tiled" to define a baffle or tuning element having a plurality of these tuning element unit cells 204 (e.g., tuning element 224 of FIG. 12). The tuning element unit cell 204 includes a plurality of partial flow ports 208 on its perimeter. When disposed in abutting relation with one or more other tuning element unit cells 204, adjoining partial flow ports 208 will collectively define a larger tuning element flow port. A protrusion 212 is centrally disposed in the tuning element unit cell 204. This protrusion is a solid, may be of any appropriate shape, and functions as a filter wall.

Figure 11B:
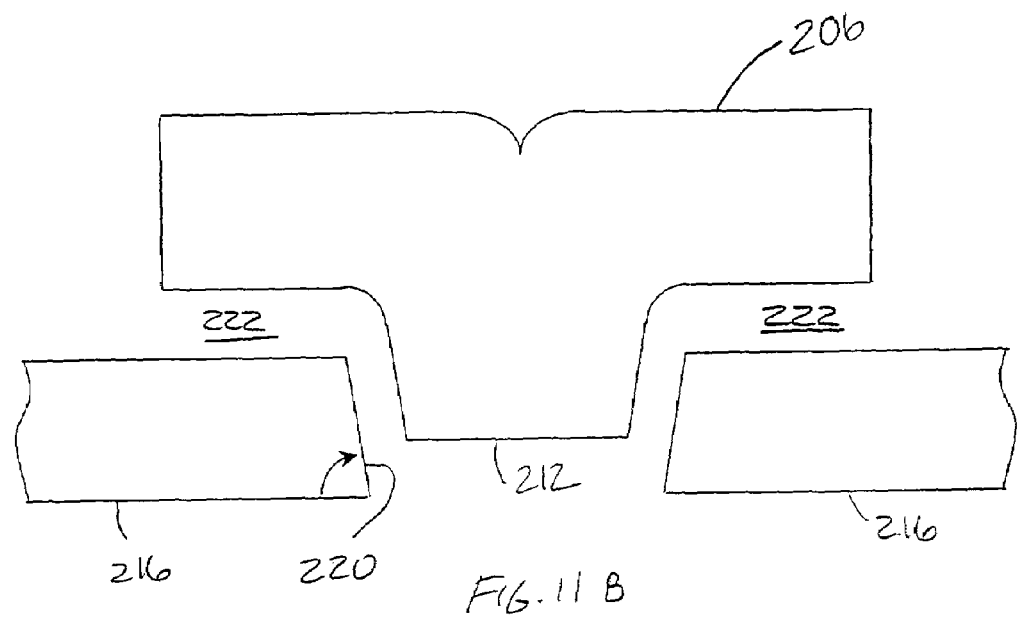
FIG. 11B is a cutaway, side view of a tuning element having a single tuning element unit cell of the configuration of FIG. 11A, where the tuning element is in a first position relative to a lower plate of a MEMS flow module.
Figure 11C:
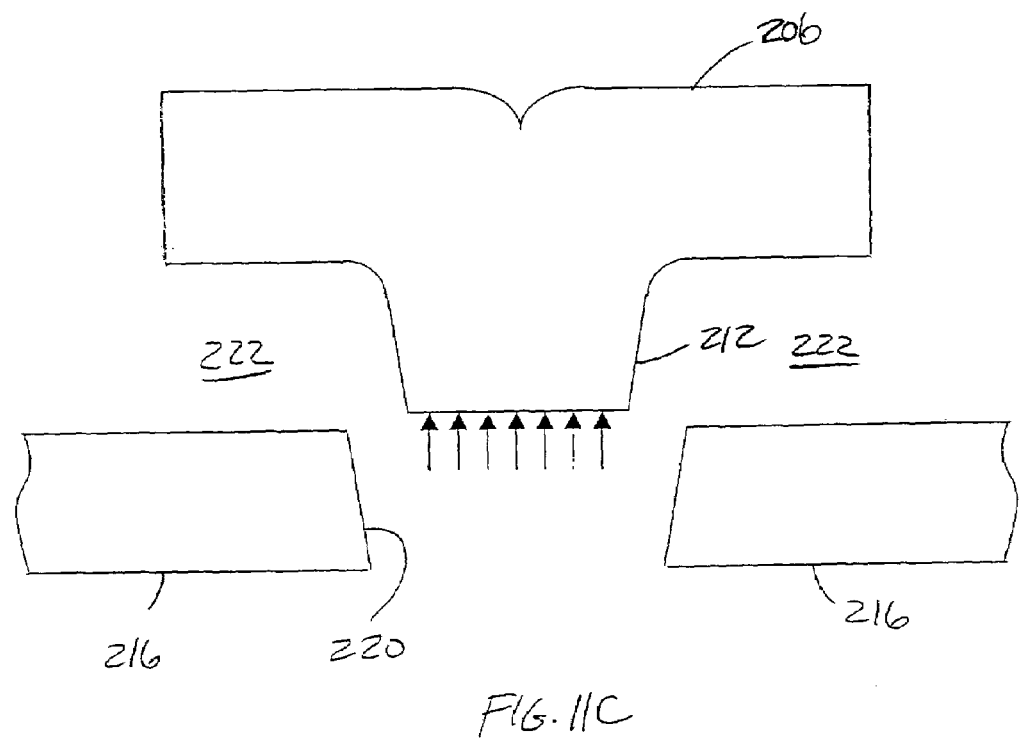
FIG. 11C is a cutaway, side view of the tuning element of FIG. 11B in a second position relative to the lower plate of the MEMS flow module that allows for an increased flow out of the MEMS flow module.

FIGS. 11B-C illustrate a baffle or tuning element 206 corresponding with a single unit cell 204. A lower plate 216 of a MEMS flow module at least generally in accordance with the foregoing includes a lower flow port 220 that is vertically aligned with the protrusion 212 on the tuning element 206. A flow channel 222 exists between the tuning element 206 and the lower plate 216 in accordance with the foregoing. Although the sidewall of the lower flow ports 220 is "slanted" in one orientation in FIGS. 11B-C, it could be disposed at any angle and including at a right angle to the upper and lower surfaces of the lower plate 216. In any case, the tuning element 206 is suspended above the lower plate 216 by one or more suspension springs (not shown) in accordance with the foregoing. The position of the tuning element 206 illustrated in FIG. 11B may correspond with the pressure acting on the tuning element 206 being below the "set point" of the MEMS flow module—that is, the pressure at which the tuning element 206 will begin to move away from the lower plate 216 to provide a pressure or flow regulation function in the above-noted manner. FIG. 11C may correspond with the tuning element 206 having moved its maximum distance from the lower plate 216. That is, FIG. 11C may correspond with the maximum height of the flow channel 222, and thereby the maximum flow rate through the MEMS flow module for a certain pressure acting on the tuning element 206 from a flow into the MEMS flow module through the lower flow port 220. The gap between the protrusion 212 and the lower plate 216 may be that which provides a filtering function for a flow proceeding through the flow channel 222 in a direction to exit the MEMS flow module through the lower flow port 220.

FIG. 12 illustrates one embodiment of a baffle, tuning element, or other flow control element 224 defined by a plurality of tuning element unit cells of the type illustrated in FIGS. 11A-C. Although a "matrix" of 9×5 unit cells 204 were tiled to define the tuning element 224, any appropriate number could be tiled per row and per column to provide a desired size/configuration. Those partial flow ports 208 on the perimeter of the various tuning element unit cells 204 that adjoin with a partial flow port 208 of at least one other tuning element unit cell 204 to define a complete tuning element flow port 226 are used by the tuning element 224. The partial flow ports 208 of those tuning element unit cells 204 disposed on a perimeter of the tuning element 224 were not formed since the flow can go around the perimeter of the tuning element 224 in the above-noted manner.

A plurality of anchors 228 of any appropriate configuration are fixed to the lower plate 216 and extend "upwardly" therefrom. A flexible beam 232 extends from each of these anchors 228 and is attached to the tuning element 224, typically by a flexible interconnect 234 (e.g. to allow at least a certain degree of relative movement between the tuning element 224 and each flexible beam 232). One flexible beam 232 is disposed on each side of the tuning element 224 in the illustrated embodiment to dispose the tuning element 224 in spaced relation to the lower plate 216, and further to allow the tuning element 224 to move toward and away from the lower plate 216 by a flexing or bending of the various flexible beams 232.

Figure 13:
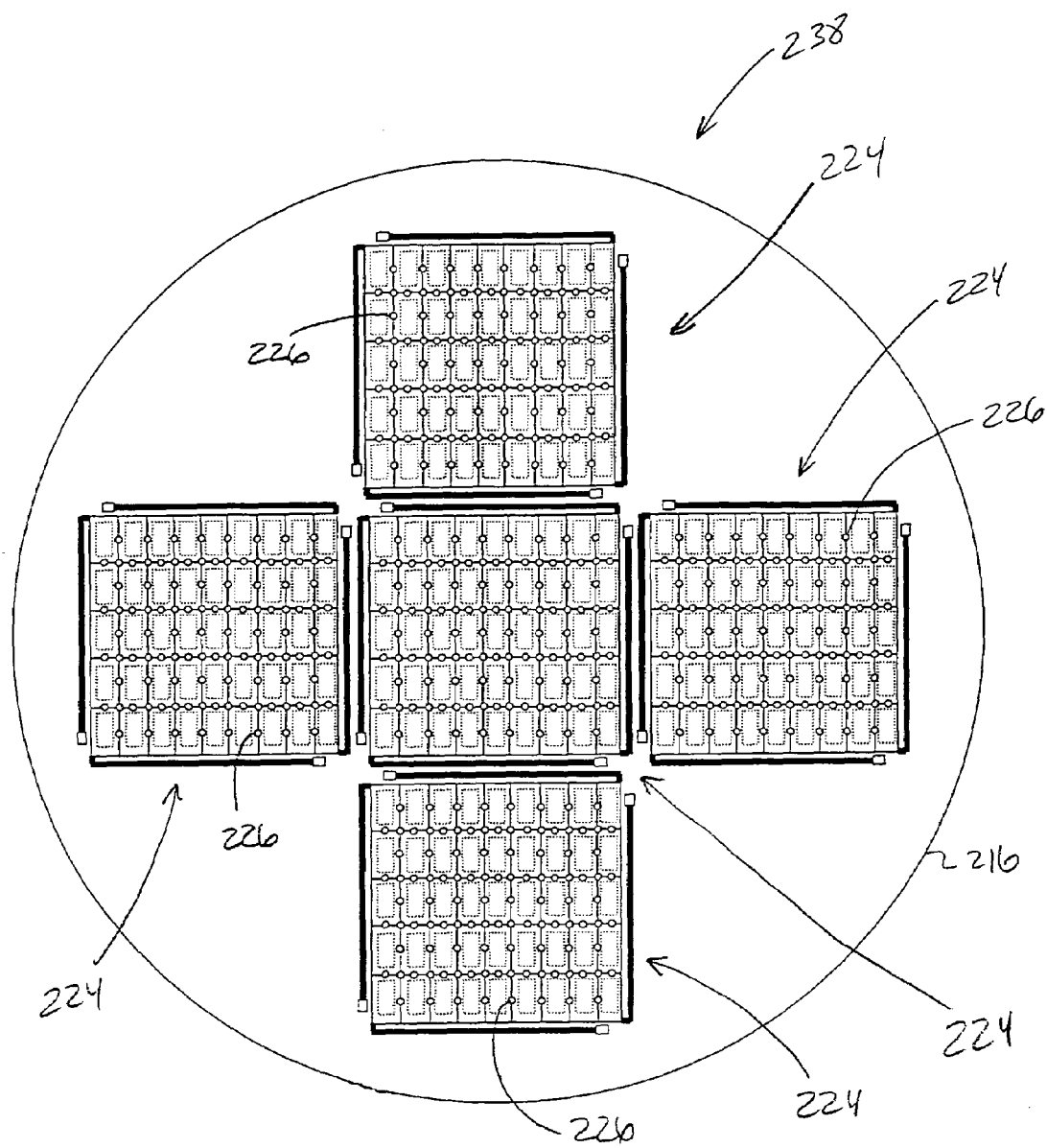
FIG. 13 is another embodiment of a MEMS flow module that uses a plurality of the tuning elements of FIG. 12.

A plurality of tuning elements 224 may be used in combination in a single MEMS flow module. One such embodiment is illustrated in FIG. 13, where a MEMS flow module 238 has five of the tuning elements 224 disposed above a common lower plate 216. Any number of tuning elements 224 may be used, and in any desired/required arrangement. The various tuning elements 224 may also be of the desired/required size (e.g., formed from any number of tuning element unit cells 204). It should be noted that the MEMS flow module 238 does not use an upper plate of any kind. The "exit" from the MEMS flow module 238 will thereby be the flow around the perimeter of the tuning elements 224 or the tuning element flow ports 226 in the various tuning elements 224. Any of the other MEMS flow modules described herein also may be used without their corresponding upper plate if desired/required by a certain application. A single second upper plate with a plurality of second flow ports could be disposed in spaced relation to the various tuning elements 224, and further could be interconnected with the lower plate 216 by one or more annular supports 54 in the above-noted manner.

As noted above, surface micromachining is the preferred fabrication technique for the various MEMS flow modules described herein. In each such MEMS flow module, each component thereof (including without limitation any upper plate, a tuning element or baffle, a lower plate, springs, any annular support) may be fabricated in a structural layer or film at a single fabrication level (e.g., in $P_1$ layer 318; in $P_2$ layer 322; in $P_3$ layer 326; in $P_4$ layer 330 (FIG. 5C discussed above)). This may define an at least generally planar layer, or an at least generally planar portion with one or more structures that extend down toward, but not to, the underlying structural layer at the underlying fabrication level. Consider the case of the upper plate 62 in the FIG. 10 embodiment. The overpressure stops 64 could be fabricated by forming the tuning element 78 in the $P_3$ layer 326, depositing the $S_4$ layer 328, forming cuts or holes in the $S_4$ layer 328 that extend all the way down to the $P_3$ layer 326, depositing sacrificial material in the bottom of these cuts or holes (the thickness of which will define the spacing between the overpressure stops 64 and the tuning element 78 illustrated in FIG. 10), and then depositing the $P_4$ layer 330 on top of the S₄ layer 328, as well as into the "partially filled" cuts or holes in the S₄ layer 328. The deposition of structural material into these "partially filled" cuts or holes in the S₄ layer 328 is then what defines the overpressure stops 64. The upper plate 62 may then be characterized as existing in a single fabrication level (P₄ layer 330 in the noted example), since it was defined by a deposition of a structural material before having to form any overlying layer of a sacrificial material (e.g., from a single deposition of a structural layer or film). It should be noted that at least part of the S₄ layer 328 remains between the entirety of the tuning element 78 and the upper plate 62 (prior to the etch release).

Each such component of the MEMS flow modules described herein could also be fabricated in multiple structural layers or films at multiple fabrication levels. For instance, the upper or lower plate of a given MEMS flow module could be fabricated in both the P₂ layer 322 and P₁ layer 318, where the P₂ layer 322 is deposited directly on the P₁ layer 318. Another option would be to form a particular component of a given MEMS flow module in multiple structural layers or films at different fabrication levels, but that are structurally interconnected in an appropriate manner (e.g., by one or more posts, columns or the like extending between). For instance, the upper plate, lower plate, or baffle/tuning element could be formed in both the P₄ layer 330 and the P₃ layer 326 discussed above in relation to FIG. 5C, with one or more structural interconnections extending therebetween (that would pass through the S₄ layer 328). Generally, this can be done by forming appropriate cuts or openings down through the S₄ layer 328 (to expose the underlying P₃ layer 326 and that will define such structural interconnections once the P₄ layer 330 is deposited therein) before depositing the P₄ layer 330.

One particularly desirable application for the flow assemblies 10, 26, and 43 of FIGS. 1-4B, as discussed above, is to regulate pressure within the anterior chamber of an eye. This is schematically illustrated in FIG. 14A. Here, an anterior chamber 242 of a patient's eye (or other body region for that matter—a first body region) is fluidly interconnected with an appropriate drainage area 244 by an implant 246. The drainage area 244 may be any appropriate location, such as externally of the eye (e.g., on an exterior surface of the cornea), within the eye (e.g., Schlemm's canal), or within the patient's body in general (a second body region).

Generally, the implant 246 includes a conduit 250 having a pair of ends 258a, 258b, with a flow path 254 extending therebetween. The size, shape, and configuration of the conduit 250 may be adapted as desired/required, including to accommodate the specific drainage area 244 being used. Representative configurations for the conduit 250 are disclosed in U.S. Patent Application Publication No. 2003/0212383, as well as U.S. Pat. Nos. 3,788,327; 5,743,868; 5,807,302; 6,626,858; 6,638,239; 6,533,768; 6,595,945; 6,666,841; and 6,736,791, the entire disclosures of which are incorporated by reference in their entirety herein.

A flow assembly 262 is disposed within the flow path 254 of the conduit 250. All flow leaving the anterior chamber 242 through the implant 246 is thereby directed through the flow assembly 262. Similarly, any flow from the drainage area 244 into the implant 246 will have to pass through the flow assembly 262. The flow assembly 262 may be retained within the conduit 250 in any appropriate manner and at any appropriate location (e.g., it could be disposed on either end 258a, 258b, or any intermediate location therebetween). The flow assembly 262 may be in the form of any of the flow assemblies 10, 26, or 43 discussed above, replacing the MEMS flow module 22 with either of the MEMS flow modules 44, 58, 86, 126, 138, 168, 238, or a MEMS flow module in accordance with FIGS. 11A-C or FIG. 12. Alternatively, the flow assembly 262 could simply be in the form of the MEMS flow modules 44, 58, 86, 126, 138, 168, 238, or a MEMS flow module in accordance with FIGS. 11A-C or FIG. 12. Any appropriate coating may be applied to at least those surfaces of the implant 246 that would be exposed to biological material/fluids, including without limitation a coating that improves biocompatibility, that makes such surfaces more hydrophilic, and/or that reduces the potential for bio-fouling. In one embodiment, a self assembled monolayer coating (e.g., poly-ethylene-glycol) is applied in any appropriate manner (e.g., liquid or vapor phase, with vapor phase being the preferred technique) to the noted surfaces.

FIG. 14B illustrates a representative embodiment in accordance with FIG. 14A. Various portions of the eye 266 are identified in FIG. 14B, including the cornea 268, iris 272, pupil 274, lens 276, anterior chamber 284, posterior chamber 286, Schlemm's canal 278, trabecular meshwork 280, and aqueous veins 282. Here, an implant or shunt 290 having an appropriately-shaped conduit 292 is directed through the cornea 268. The conduit 292 may be in any appropriate form, but will typically include at least a pair of ends 294a, 294b, as well as a flow path 296 extending therebetween. End 294a is disposed on the exterior surface of the cornea 268, while end 294b is disposed within the anterior chamber 284 of the eye 266.

A flow assembly 298 is disposed within the flow path 296 of the conduit 292. All flow leaving the anterior chamber 284 through the shunt 290 is thereby directed through the flow assembly 298. Similarly, any flow from the environment back into the shunt 290 will have to pass through the flow assembly 298 as well. The flow assembly 298 may be retained within the conduit 292 in any appropriate manner and at any appropriate location (e.g., it could be disposed on either end 294a, 294b, or any an intermediate location therebetween). The flow assembly 298 may be in the form of any of the flow assemblies 10, 26, or 43 discussed above, replacing the MEMS flow module 22/42 with either of the MEMS flow modules 44, 58, 86, 126, 138, 168, 238, or a MEMS flow module in accordance with FIGS. 11A-C or FIG. 12. Alternatively, the flow assembly 298 could simply be in the form of the MEMS flow modules 44, 58, 86, 126, 138, 168, 238, or a MEMS flow module in accordance with FIGS. 11A-C or FIG. 12. Any appropriate coating may be applied to at least those surfaces of the shunt 290 that would be exposed to biological material/fluids, including without limitation a coating that improves biocompatibility, that makes such surfaces more hydrophilic, and/or that reduces the potential for bio-fouling. In one embodiment, a self assembled monolayer coating (e.g., poly-ethylene-glycol) is applied in any appropriate manner (e.g., liquid or vapor phase, with vapor phase being the preferred technique) to the noted surfaces.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An implant for addressing pressure within a first body region, said implant comprising:
a conduit comprising a flow path and adapted to fluidly interconnect with the first body region; and
a MEMS flow module disposed within said flow path, wherein said MEMS flow module comprises:
a flow regulator, wherein said flow regulator comprises a first baffle; and
a first plate, wherein said first plate comprises a first flow port, wherein said first baffle is aligned with said first flow port, and wherein said first baffle is movable relative to said first plate to change a magnitude of a spacing of said first baffle from said first plate in response to a change in differential pressure across said MEMS flow module;
wherein the first plate comprises a first group of a plurality of the first flow ports and wherein the first baffle is aligned with each first flow port in the first group; and
wherein said first baffle comprises a plurality of baffle flow ports, wherein said plurality of first flow ports in said first group and said plurality of baffle flow ports are arranged such that a flow through any given said first flow port must change direction to flow through any of said plurality of baffle flow ports.

2. An implant, as claimed in claim 1, wherein: said first baffle is movable along an axis that corresponds with a direction of a flow entering said MEMS flow module through said first flow port.

3. An implant, as claimed in claim 1, wherein: said first baffle is always disposed in spaced relation to said first plate.

4. An implant, as claimed in claim 1, further comprising: at least one spring movably interconnecting said first baffle with said first plate.

5. An implant, as claimed in claim 1, further comprising: a plurality of springs movably interconnecting said first baffle with said first plate.

6. An implant, as claimed in claim 1, further comprising: a first flow channel defined by a space between said first baffle and said first plate, wherein at least a portion of said flow entering said MEMS flow module through said first flow port flow passes through said first flow channel before exiting said MEMS flow module.

7. An implant, as claimed in claim 1, wherein: during any movement of said first baffle relative to said first plate, a distance between said first baffle and said first plate is proportional across an entire extent of said first baffle.

8. An implant, as claimed in claim 1, wherein: all flow though any of said first flow ports in said first group is required to proceed around a perimeter of said first baffle.

9. An implant, as claimed in claim 1, wherein: said first baffle is disposed to change a direction of said flow entering said MEMS flow module through said first flow port before said flow exits said MEMS flow module.

10. An implant, as claimed in claim 9, wherein: said flow entering said MEMS flow module exerts a normal force on said first baffle.

11. An implant, as claimed in claim 1, wherein: said MEMS flow module is a passive device.

12. An implant, as claimed in claim 1, wherein: the first body region is an anterior chamber of an eye.

13. An implant for addressing pressure within a first body region, said implant comprising:
a conduit comprising a flow path and adapted to fluidly interconnect with the first body region; and
a MEMS flow module disposed within said flow path, wherein said MEMS flow module comprises:
a flow regulator, wherein said flow regulator comprises a first baffle; and
a first plate, wherein said first plate comprises a first flow port, wherein said first baffle is aligned with said first flow port, and wherein said first baffle is movable relative to said first plate to change a magnitude of a spacing of said first baffle from said first plate in response to a change in differential pressure across said MEMS flow module; and
means for limiting a maximum amount of movement of said first baffle away from said first flow port.

14. An implant, as claimed in claim 13, wherein: said first baffle comprises a plurality of baffle flow ports, wherein said plurality of first flow ports in said first group and said plurality of baffle flow ports are arranged such that a flow through any given said first flow port must change direction to flow through any of said plurality of baffle flow ports.

15. An implant, as claimed in claim 13, wherein said MEMS flow module further comprises a plurality of said first baffles and at least one spring separately interconnecting each said first baffle with said first plate, wherein at least one said first flow port is associated with each said first baffle.

16. An implant, as claimed in claim 13, further comprising: at least one spring movably interconnecting said first baffle and said first plate; a second plate comprising a second flow port and that is spaced from said first baffle, wherein said first baffle is located between said first and second plates, and wherein at least a portion of said flow that enters said MEMS flow module through said first flow port exits said MEMS flow module through said second flow port; and an annular support interconnecting said first and second plates, wherein said first plate, said second plate, and said annular support collectively define an enclosed space.

17. An implant, as claimed in claim 16, wherein: said second plate comprises at least one overpressure stop aligned with said first baffle.

18. An implant for addressing pressure within a first body region, said implant comprising:
a conduit comprising a flow path and adapted to fluidly interconnect with the first body region; and
a MEMS flow module disposed within said flow path, wherein said MEMS flow module comprises:
a flow regulator, wherein said flow regulator comprises a first baffle; and
a first plate, wherein said first plate comprises a first flow port, wherein said first baffle is aligned with said first flow port, and wherein said first baffle is movable relative to said first plate to change a magnitude of a spacing of said first baffle from said first plate in response to a change in differential pressure across said MEMS flow module;
wherein: said first baffle exists at least in a first fabrication level and said first plate exists at least in a second fabrication level that is spaced from said first fabrication level.

19. An implant, as claimed in claim 18, wherein: a position of said first baffle within said MEMS flow module is dependent upon a pressure being exerted on said first baffle by a flow entering said MEMS flow module through said first flow port, wherein a flow rate of said flow exiting said MEMS flow module is dependent upon a position of said first baffle within said MEMS flow module, and wherein said first baffle changes a direction of said flow entering said MEMS flow module through said first flow port before said flow exits said MEMS flow module.

20. An implant, as claimed in claim 18,
   wherein: said first baffle moves relative to said first plate so as to provide greater than a proportional increase in a flow rate out of said MEMS flow module for an increase in differential pressure across said MEMS flow module.

21. An implant, as claimed in claim 18,
   wherein: a position of said first baffle is dependent upon a pressure being exerted on said first baffle by said flow entering said MEMS flow module through said first flow port, and wherein a flow rate of said flow exiting said MEMS flow module is dependent upon a position of said first baffle.

22. An implant, as claimed in claim 21, wherein said first baffle is movably suspended beyond said first plate and in overlying relation to said first flow port, wherein a spacing between said first baffle and said first plate defines a first flow channel, wherein a flow entering said MEMS flow module through said first flow port is forced by said first baffle to proceed through said first flow channel, and wherein a magnitude of said spacing between said first baffle and said first plate is variable and dependent upon a pressure being exerted on said first baffle by said flow entering said MEMS flow module through first flow port.

23. An implant, as claimed in claim 18,
   wherein: said first baffle is in contact with said first plate until a certain differential pressure across said MEMS flow module is reached.

24. An implant, as claimed in claim 18, further comprising: a first housing associated with said MEMS flow module, wherein said first housing and said MEMS flow module are collectively disposed within said flow path.

25. An implant, as claimed in claim 24, further comprising: a self-assembled monolayer coating on all surfaces of said first housing that may be exposed to a biological material or a biological fluid when said implant is installed.

26. An implant, as claimed in claim 25, wherein: said self-assembled monolayer coating is poly-ethylene-glycol.

27. An implant for addressing pressure within a first body region, said implant comprising:
   a conduit comprising a flow path and adapted to fluidly interconnect with the first body region; and
   a MEMS flow module disposed within said flow path, wherein said MEMS flow module comprises:
      a flow regulator, wherein said flow regulator comprises a first baffle; and
      a first plate, wherein said first plate comprises a first flow port, wherein said first baffle is aligned with said first flow port, and wherein said first baffle is movable relative to said first plate to change a magnitude of a spacing of said first baffle from said first plate in response to a change in differential pressure across said MEMS flow module;
      a self-assembled monolayer coating on all surfaces of said MEMS flow module that may be exposed to a biological material or a biological fluid when said implant is installed.

28. A tunable shunt for permitting flow of fluid from between an anterior chamber of an eye and an exterior of the eye, the shunt comprising:
   a housing adapted to be implanted, at least in part, in the eye;
   a conduit disposed within the housing and defining a flow path; and
   a MEMS flow module disposed within the flow path, wherein the MEMS flow module further includes:
      a flow regulator having a first baffle; and
      a first plate defining a first flow port;
      wherein the first baffle is aligned with the first flow port, and
      wherein the first baffle is movable relative to the first plate in response to a change in differential pressure across said MEMS flow module; and
      wherein a position of the first baffle is dependent upon a pressure being exerted on the first baffle by the flow entering the MEMS flow module through the first flow port, and
      wherein a flow rate of the flow exiting said MEMS flow module is dependent upon a position of the first baffle;
      wherein the first baffle exists at least in a first fabrication level and the first plate exists at least in a second fabrication level that is spaced from the first fabrication level.

29. The tunable shunt set forth in claim 28 wherein the first baffle is always disposed in spaced relation to the first plate.

30. The tunable shunt set forth in claim 28 wherein the first baffle is in contact with the first plate until a certain differential pressure across the MEMS flow module is reached.

31. The tunable shunt set forth in claim 28 further comprising at least one spring operably interconnected with the first baffle and the first plate.

32. The tunable shunt set forth in claim 28 wherein the first plate further defines a plurality of first flow ports and wherein the flow regulator comprises a plurality of first baffles, wherein at least one of the first baffles is aligned with at least one of the first flow ports such that flow through such first flow port must change direction.

33. The tunable shunt set forth in claim 28 further comprising means for limiting the maximum amount of movement of the first baffle away from the first flow port.

34. The tunable shunt set forth in claim 28 further comprising:
   a second plate defining a second flow port and connected to the first plate such that the baffle is disposed between the first plate and the second plate;
   at least one spring operably interconnected with the first baffle and the first plate; and
   means for limiting the maximum amount of movement of the first baffle away from the first flow port;
   wherein the first plate further defines a plurality of first flow ports and wherein the flow regulator comprises a plurality of first baffles;
   wherein at least one of the first baffles is aligned with at least one of the first flow ports such that flow through such first flow port must change direction; and
   wherein the first baffle exists at least in a first fabrication level and the first plate exists in a second fabrication level that is spaced from the first fabrication level; and
   wherein the first baffle moves relative to the first plate so as to provide greater than a proportional increase in a flow rate out of the MEMS flow module for an increase in differential pressure across the MEMS flow module.

35. The tunable shunt of claim 28 further comprising a biocompatible coating on at least portions of the MEMS flow module.

* * * * *